(12) United States Patent
John et al.

(10) Patent No.: US 11,142,505 B2
(45) Date of Patent: Oct. 12, 2021

(54) COMPOSITIONS FOR APP-SELECTIVE BACE INHIBITION AND USES THEREFOR

(71) Applicant: The Regents of the University of California, Oakland, CA (US)

(72) Inventors: Varghese John, Culver City, CA (US); Patricia Spilman, Culver City, CA (US); Barbara Jagodzinska, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 332 days.

(21) Appl. No.: 15/755,496

(22) PCT Filed: Aug. 29, 2016

(86) PCT No.: PCT/US2016/049271
§ 371 (c)(1),
(2) Date: Feb. 26, 2018

(87) PCT Pub. No.: WO2017/035529
PCT Pub. Date: Mar. 2, 2017

(65) Prior Publication Data
US 2019/0077766 A1 Mar. 14, 2019

Related U.S. Application Data

(60) Provisional application No. 62/210,945, filed on Aug. 27, 2015.

(51) Int. Cl.
| | |
|---|---|
| *A61P 25/28* | (2006.01) |
| *C07D 233/88* | (2006.01) |
| *C07D 401/04* | (2006.01) |
| *C07D 401/06* | (2006.01) |
| *C07D 401/10* | (2006.01) |
| *C07D 401/14* | (2006.01) |
| *C07D 403/04* | (2006.01) |
| *C07D 403/06* | (2006.01) |
| *C07D 403/08* | (2006.01) |
| *C07D 403/10* | (2006.01) |
| *C07D 403/12* | (2006.01) |
| *C07D 405/10* | (2006.01) |
| *C07D 405/12* | (2006.01) |
| *C07D 405/14* | (2006.01) |
| *C07D 409/04* | (2006.01) |
| *C07D 413/04* | (2006.01) |
| *C07D 413/10* | (2006.01) |
| *C07D 417/04* | (2006.01) |
| *A61K 31/4166* | (2006.01) |
| *A61K 31/4178* | (2006.01) |

(52) U.S. Cl.
CPC ............ *C07D 233/88* (2013.01); *A61P 25/28* (2018.01); *C07D 401/04* (2013.01); *C07D 401/06* (2013.01); *C07D 401/10* (2013.01); *C07D 401/14* (2013.01); *C07D 403/04* (2013.01); *C07D 403/06* (2013.01); *C07D 403/08* (2013.01); *C07D 403/10* (2013.01); *C07D 403/12* (2013.01); *C07D 405/10* (2013.01); *C07D 405/12* (2013.01); *C07D 405/14* (2013.01); *C07D 409/04* (2013.01); *C07D 413/04* (2013.01); *C07D 413/10* (2013.01); *C07D 417/04* (2013.01)

(58) Field of Classification Search
CPC combination set(s) only.
See application file for complete search history.

(56) References Cited

U.S. PATENT DOCUMENTS

| | | | |
|---|---|---|---|
| 2005/0282825 A1* | 12/2005 | Malamas | ................ A61P 25/00 514/256 |
| 2007/0004730 A1* | 1/2007 | Zhou | .................... C07D 401/04 514/242 |
| 2007/0004786 A1 | 1/2007 | Malamas et al. | |
| 2007/0072925 A1 | 3/2007 | Malamas et al. | |
| 2015/0282825 A1 | 10/2015 | Trees et al. | |
| 2019/0077766 A1 | 3/2019 | John et al. | |
| 2021/0101879 A1 | 4/2021 | Varghese et al. | |

FOREIGN PATENT DOCUMENTS

| | | |
|---|---|---|
| AU | 2016311502 B2 | 7/2019 |
| CA | 2 996 542 A1 | 3/2017 |
| CN | 1968945 A | 5/2007 |
| CN | 101213183 A | 7/2008 |
| CN | 101273018 A | 9/2008 |
| CN | 101663281 A | 3/2010 |
| CN | 108349905 A | 7/2018 |
| EP | 3 341 362 A4 | 7/2018 |
| JP | 2008-503459 A | 2/2008 |
| JP | 2009-500329 A | 1/2009 |
| JP | 2009/500329 A | 1/2009 |
| JP | 2018-525447 A | 9/2018 |
| KR | 10-2018-0090778 A | 8/2018 |

(Continued)

OTHER PUBLICATIONS

Malamas et al. Bioorg. Med. Chem. Lett. 2010, 20, 6597. (Year: 2010).*
First Examination Report received in Australian Patent Application No. 2016311502, dated Sep. 25, 2018, 7 pages.
Malamas et al, "Design and Synthesis of 5,5'-Disubstituted Aminohydantoins as Potent and Selective Human β-Secretase (BACE1) Inhibitors", Journal of Medicinal Chemistry, 2010, vol. 53, No. 3, pp. 1146-1158.
Malamas et al, "Design and synthesis of aminohydantoins as potent and selective human β-secretase (BACE1) inhibitors with enhanced brain permeability", Bioorganic and Medicinal Chemistry Letters, 2010, vol. 20, No. 22, pp. 6597-6605.

(Continued)

*Primary Examiner* — Amanda L. Aguirre
(74) *Attorney, Agent, or Firm* — Foley Hoag LLP

(57) ABSTRACT

Selected compounds, compositions, and methods for inhibiting BACE are presented that have relatively high selectivity towards APP via interaction of the inhibitor with both BACE and APP.

20 Claims, 12 Drawing Sheets

(56) References Cited

FOREIGN PATENT DOCUMENTS

| WO | 2007/005404 A1 | 1/2007 | |
|---|---|---|---|
| WO | WO-2007/078813 A2 | 7/2007 | |
| WO | 2008-118379 A2 | 10/2008 | |
| WO | 2014/127042 A1 | 8/2014 | |
| WO | 2017/035529 A1 | 3/2017 | |
| WO | WO-2017/035529 A9 | 8/2017 | |
| WO | WO-2019/005297 A1 | 1/2019 | |
| WO | WO-2019169183 A1 * | 9/2019 | ........... C07D 233/70 |

OTHER PUBLICATIONS

Second Examination Report received in Australian Patent Application No. 2016311502, dated Apr. 15, 2019, pp. 2.

Extended European Search Report for European Patent Application No. 16840254.3 dated May 10, 2019, pp. 8.

ISA/KR, International Search Report and Written Opinion, completed Dec. 20, 2016 for PCT Application No. PCT/US2016/049271, 17 pages.

J. Med. Chem., 2010, 53 (3), pp. 1146-1158: Michael S. Malamas et al.; Design and Synthesis of 5,5'-Disubstituted Aminohydantoins as Potent and Selective Human β-Secretase (BACE1) Inhibitors.

Bioorganic & Medicinal Chemistry Letters vol. 20, Issue 22, Nov. 15, 2010, pp. 6597-6605: Michael S. Malamas et al.; Design and synthesis of aminohydantoins as potent and selective human β-secretase (BACE1) inhibitors with enhanced brain permeability.

Notice of Reasons for Refusal received for Japanese Patent Application Serial No. 2018-530646 dated Jun. 23, 2020, 10 pages (Including English translation).

International Preliminary Report on Patentability received for PCT Application Serial No. PCT/US2016/049271 dated Dec. 28, 2017, 23 pages.

First Office Action received for Chinese Patent Application Serial No. 201680053449.1 dated Oct. 13, 2020, 16 pages (Including English Translation).

Cheron et al., "Effect of sampling on BACE-1 ligands binding free energy predictions via MM-PBSA calculations," Journal of Computational Chemistry, 38(22):1941-1951 (2017).

Cruz et al., "2D QSAR studies on series of human beta-secretase (BACE-1) inhibitors," Medicinal Chemistry, 10(2):162-173 (2014).

Cumming et al., "Structure based design of iminohydantoin BACE1 inhibitors: identification of an orally available, centrally active BASE1 inhibitor," Bioorganic & Medicinal Chemistry Letters, 22(7):2444-2449 (2012).

International Search Report and Written Opinion for International Application No. PCT/US2019/020125 dated Jun. 12, 2019.

Jain et al., "Quantitative structure activity relationship analysis of aminoimidazoles as BACE-1 inhibitors," Medicinal Chemistry Research, 22(4):1740-1746 (2012).

Malamas et al., "New pyrazolyl and thienyl aminohydantoins as potent BACE1 inhibitors: Exploring the S2' region," Bioorganic & Medicinal Chemistry Letters, 21(18):5164-5170 (2011).

* cited by examiner

FAH-65
MW: 423

FAH-66
MW: 440

FAH-74
MW: 409

BACE IC50 = 0.009uM

COMPOSITIONS FOR APP-SELECTIVE BACE INHIBITION AND USES THEREFOR

This application claims priority to our US provisional application having Ser. No. 62/210,945, which was filed 27 Aug. 15 and which is incorporated by reference herein.

FIELD OF THE INVENTION

The field of the invention is enzyme inhibitors and methods therefor, particularly as it relates to APP (amyloid precursor protein)-specific BACE (beta-secretase) inhibitors.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

BACE inhibitors have gained significant attention due to the discovery that a mutation in the APP appears to protect against Alzheimer's Disease and other age-related cognitive decline. More specifically, the mutation is at the P2' residue of the BACE cleavage site and results in a significantly reduced Aβ production. Unfortunately, the substrate specificity of BACE is not exclusively limited to APP, and complete inhibition of BACE would thus have adverse effects.

More recently, certain BACE inhibitors with at least some selectivity towards BACE were reported as is disclosed in WO 2014/127042, US 2016/0159746, and US 2014/0371283. While such inhibitors had desirable selectivity against BACE with respect to APP, relatively high concentrations were required for inhibition. Moreover, many of the compounds failed to penetrate the blood brain barrier.

Thus, despite the relatively detailed knowledge of BACE activity and its substrate APP, various drawbacks still remain for known BACE inhibitors, especially high IC50 and/or lack of penetrability across the blood brain barrier. Therefore, there is still a need to provide improved BACE inhibitors and methods.

SUMMARY OF THE INVENTION

The present inventive subject matter is drawn to various compounds, compositions, and methods of BACE inhibition, and particularly to compounds and compositions that interact with both BACE and APP to so increase selectivity of the inhibitor. Moreover, compounds presented herein exhibit desirably low IC50 values and penetrability across the blood brain barrier.

In one aspect of the inventive subject matter, the inventors contemplate a compound that has a structure according to Formula I

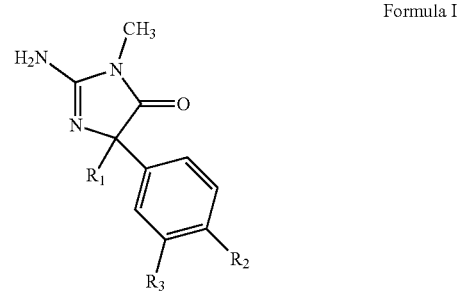

Formula I wherein $R_1$ is phenyl substituted with (i) an alkoxyalkyl, (ii) an N-alkylalkyl, or (iii) a optionally halogenated heteroaryl (e.g., pyridinyl, pyrimidinyl, or oxazolyl), or wherein $R_1$ is a halogenated heteroaryl. $R_2$ is preferably an optionally halogenated lower alkoxy group (e.g., difluoromethoxy group) or an optionally halogenated N-alkylamino group, and $R_3$ is most preferably H, halogen, or optionally halogenated lower alkyl. Therefore, suitable compounds may have a structure according to Formula II or III

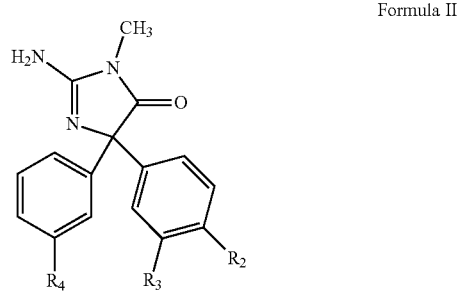

Formula II

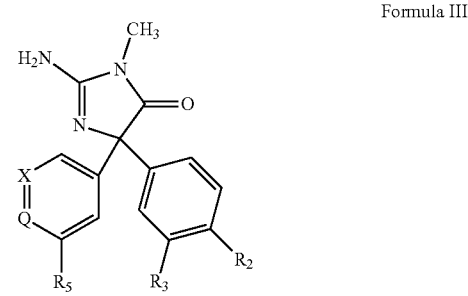

Formula III wherein $R_2$ and $R_3$ are as defined above, and wherein $R_4$ is an optionally halogenated pyridinyl, pyrimidinyl, or oxazolyl, and wherein $R_4$ is halogen (e.g., F). In especially preferred aspects, the compounds will have a structure according to any one of Formulae IV-XII Formula IV
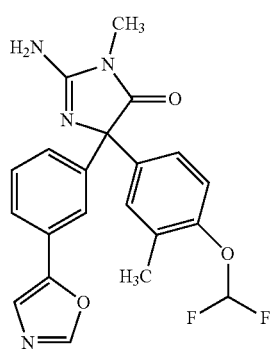
Formula V
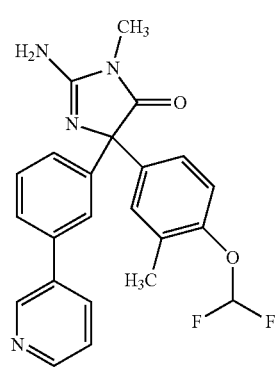
Formula VI
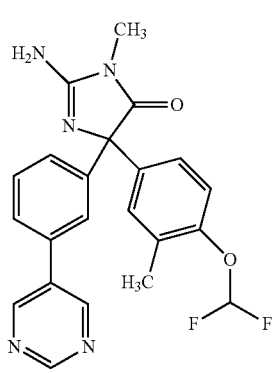
Formula VII
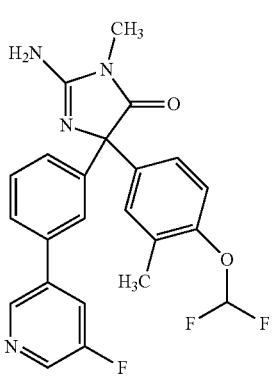
Formula VIII
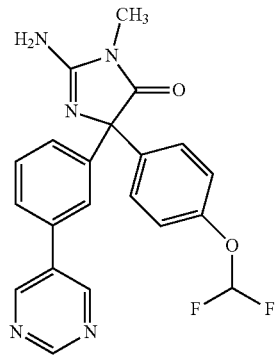
Formula IX
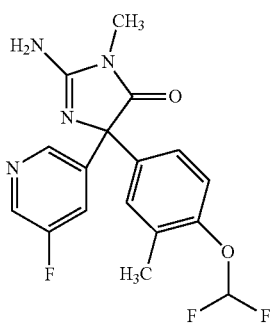
Formula X
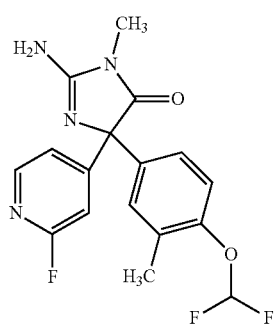
Formula XI
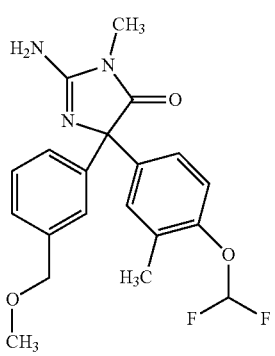

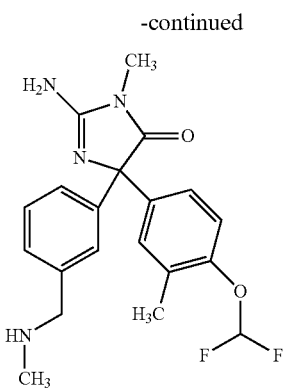

Formula XII

Consequently, the inventors also contemplate a pharmaceutical composition comprising a compound contemplated herein in combination with a pharmaceutically acceptable carrier. Most typically, the compound will be present in an amount effective to inhibit BACE in a patient when administered (e.g., orally or via injection) to the patient. As will be readily appreciated, a such formulations have BACE inhibitory activity, they will be suitable (alone or in combination with another pharmaceutical agent) for treatment of a neurological condition, and particularly for treatment of Alzheimer's Disease.

Viewed from another perspective, the inventors also contemplate the use of contemplated compounds in the manufacture of a medicament, especially where the medicament is used in the treatment of a neurodegenerative disease, and/or where the medicament is for the reduction of selective BACE activity in a patient. Consequently, BACE inhibitors and uses thereof are also specifically contemplated herein and particularly include treatment of neurological conditions (e.g., Alzheimer's Disease). Thus, the inventors also contemplate treating a patient diagnosed with Alzheimer's Disease or at risk for disease progression of mild cognitive decline.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
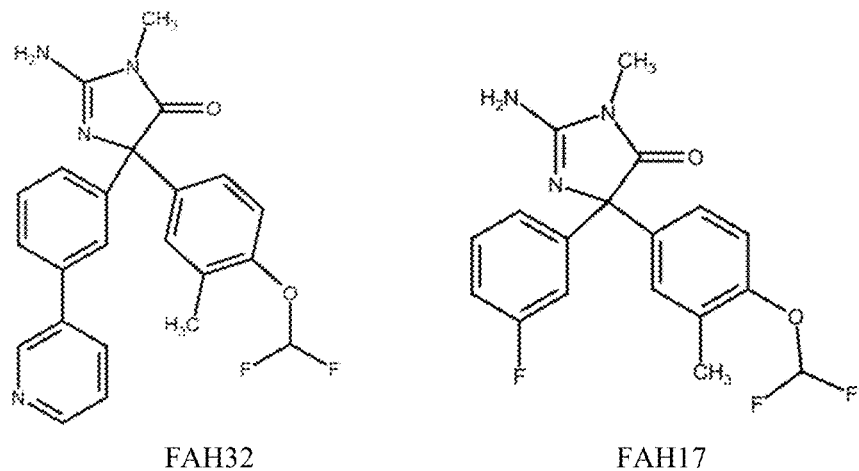
FIG. 1A depicts exemplary compounds according to the inventive subject matter.

The inventors have discovered that certain compounds as further described in more detail below had improved parameters with respect to BACE inhibition. Most notably, several of these compounds also exhibited penetrance across the blood brain barrier and preferentially inhibited BACE with respect to APP as substrate.

The improved BACE inhibitors as contemplated herein will generally have a structure according to Formula I

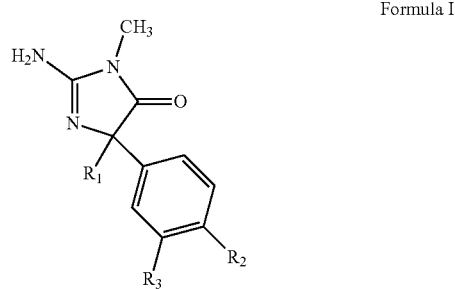

Formula I wherein $R_1$ is typically a substituted aryl or heteroaryl group, and most preferably a phenyl substituted with (i) an alkoxyalkyl, (ii) an N-alkylalkyl, or (iii) an optionally halogenated heteroaryl, or $R_1$ is a halogenated heteroaryl. In further preferred aspects, $R_2$ is an optionally halogenated lower alkoxy group (typically having 1-3 carbon atoms), an optionally halogenated N-alkylamino group (typically having 1-3 carbon atoms), an OH group, a CN group, etc. In still further preferred aspects, $R_3$ will be H, a halogen, or an optionally halogenated lower alkyl (typically having 1-3 carbon atoms).

For example, wherein $R_1$ is a phenyl, it is preferred that the phenyl is substituted with a radical that includes a heteroatom, and most preferably an oxygen or nitrogen that is separated from the phenyl by one carbon atom. Among other suitable radicals it is therefore contemplated that the phenyl may be substituted with an alkoxyalkyl (e.g., methoxymethyl) group or a N-alkylalkyl (N-methyl methyl) group. Alternatively, the phenyl in $R_1$ may also be substituted with an optionally halogenated heteroaryl. While numerous heterarul groups are deemed suitable, especially preferred heteroaryl groups will be five- or six-membered ring systems with one or two heteroatoms (e.g., N and/or O). Consequently, suitable heteroaryl groups include pyridinyl, pyrimidinyl, and oxazolyl groups.

In further contemplated aspects, R1 may also be a halogenated heteroaryl. Most typically, the heteroaryl will be a five- or six-membered ring and include one, two, or three heteroatoms. For example, suitable heteroaryl rings include imidazole, pyridine, pyrimidine, etc. With respect to the halogen substituent it is generally preferred that the halogen is fluorine or chlorine, and most typically fluorine.

R2 in most preferred compounds will be a halogenated alkoxy group, and most typically will have 1-3 carbon atoms. For example, especially preferred R2 groups will be a halogenated methoxy group, and especially a fluoromethoxy, difluoromethoxy, or trifluoromethoxy group. Alternatively, R2 may also be a relatively small substituent, including halogens, a methyl group, a CN group, or hydrogen. Likewise, R3 is preferably a relatively small substituent and may be hydrogen, lower alkyl (between 1-3 carbon atoms), CN, or a halogen.

Therefore, in further contemplated aspects of the inventive subject matter, contemplated compounds may also have a structure according to Formula II

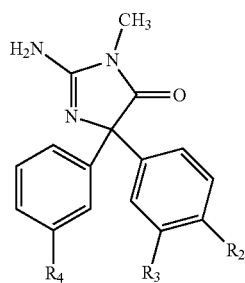

Formula II wherein $R_2$ is an optionally halogenated lower alkoxy group as described above or an optionally halogenated N-alkylamino group as described above. For example, an especially preferred $R_2$ group includes a halogenated methoxy group, particularly a difluoromethoxy group. Similarly, it is preferred that $R_3$ may be a hydrogen, a halogen (and especially fluorine or chlorine), or an optionally halogenated lower alkyl as described above. In further preferred compounds, $R_4$ is an optionally halogenated pyridinyl, pyrimidinyl, or oxazolyl. Where $R_4$ is halogenated, it is typically preferred that the halogen radical is a fluorine or chlorine radical. Moreover, it should be noted that while a single halogen is generally preferred, two, three, or more halogens are also expressly contemplated.

Where $R_1$ of Formula I is a heteroaryl, it is generally preferred that the heteroaryl will comprise one or two heteroatoms (preferably nitrogen and/or oxygen), and that the heteroaryl is a five- or six-membered ring. Particularly preferred compounds will therefore have a structure according to Formula III

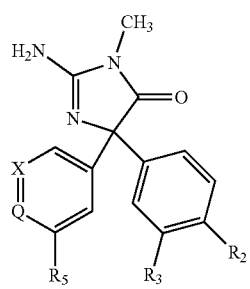

Formula III in which $R_2$ is an optionally halogenated lower alkoxy group (e.g., difluoromethoxy group) or an optionally halogenated N-alkylamino group as already described above. With respect to $R_3$ it is generally contemplated that this $R_3$ is H, halogen, or an optionally halogenated lower alkyl (e.g., optionally fluorinated methyl). $R_5$ is a halogen, and most typically a fluorine or chlorine radical. Moreover, it is noted that the heteroaryl may be further halogenated with one or more additional halogen radicals. In the compound of Formula III, X and Q are typically independently CH or N, and X and Q are not the same. However, one or more other heteroatoms (including S and Se) are also expressly contemplated.

Consequently, especially preferred compounds according to the inventive subject matter will include those shown below having a structure according to Formulae IV-XIII

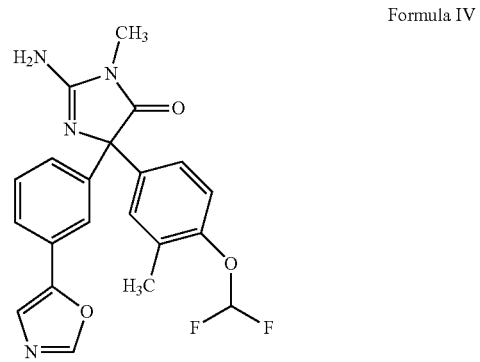

Formula IV

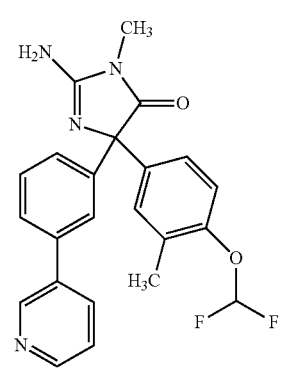

Formula V

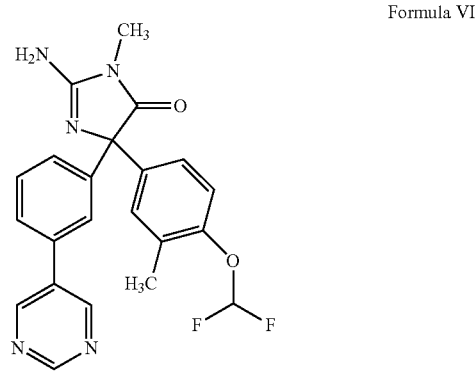 [SMILES: Cc1cc(C2(C3CCCC(c4cncnc4)C3)N=C(N)N(C)C2=O)ccc1OC(F)F]

Formula VI

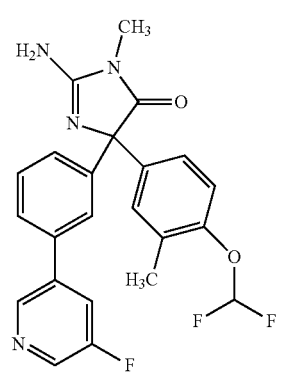

Formula VII

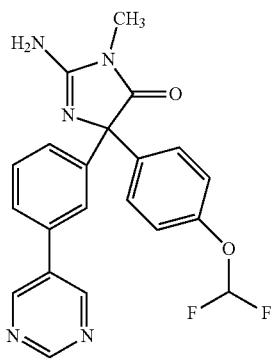

Formula VIII

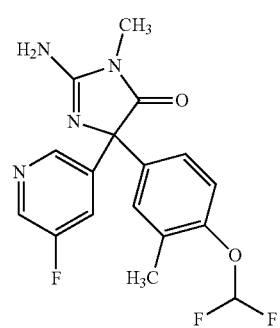

Formula IX

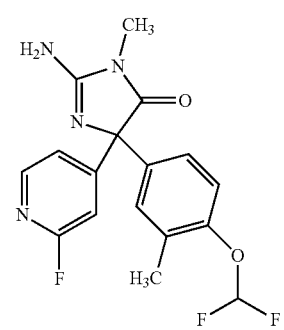

Formula X

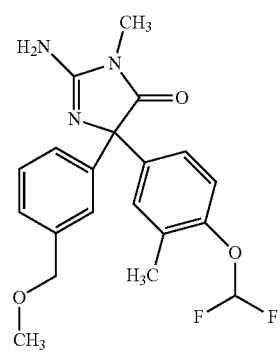

Formula XI

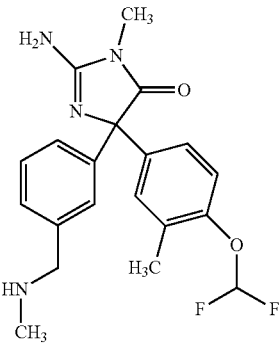

Formula XII

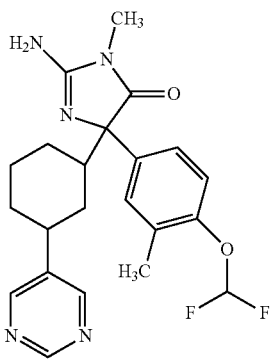

Formula XIII

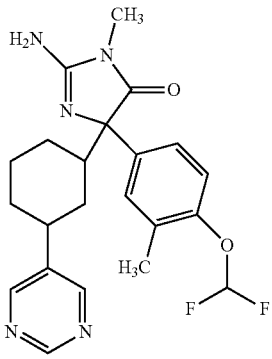

In further contemplated aspects, it is noted the compounds according to Formulae I-XIII may include aryl or heteroaryl groups other than those specified above, and suitable alternative aryl or heteroaryl groups include aromatic monocyclic or polycyclic groups, typically comprising between 5 and 18 carbon ring members, which may be unsubstituted or substituted by one or more suitable substituents, and which may be further fused one or more cycloalkyl groups, heterocycloalkyl groups, or heteroaryl groups (which themselves may be unsubstituted or substituted by one or more suitable substituents). Examples for aryl groups include phenyl, biphenyl, 1,2,3,4-tetrahydronaphthyl, naphthyl, anthryl, and phenanthryl. Suitable heteroaryl groups will typically include aromatic monocyclic or polycyclic groups comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examplary heteroaryl gropus include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

In general, the various moieties or functional groups for variables in the formulae may be substituted by one or more suitable "substituents". The term "substituent" or is intended to mean any suitable substituent that may be recognized or selected, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano;

amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like. The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted). Furthermore it should be noted that the compounds contemplated herein may be prepared as prodrugs. The term "prodrug" as used herein refers to a modification of contemplated compounds, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

Of course, it should be appreciated that (where appropriate) contemplated compounds may have one or more asymmetric centers or groups that may give rise to isomeric, tautomeric, or other steric isoforms (e.g., R-, and/or S-configuration, E/Z configuration, tautomeric isoforms, enantiomers, diastereomers, etc.), and each of such forms and mixtures thereof are expressly contemplated herein.

In further contemplated aspects, the compounds may be formulated into a pharmaceutical composition, typically in combination with a pharmaceutically acceptable carrier. Preferably, the compound will be present at a concentration effective to treat Alzheimer's Disease or signs and/or symptoms associated with Alzheimer's Disease. Viewed from another perspective, it is also contemplated that the compounds will be present in the pharmaceutical composition in an amount effective to reduce BACE activity in a patient when the formulation is administered to the patient. Therefore, contemplated compounds and pharmaceutical compositions will also be advantageous in reducing Aβ level in neuronal tissue and associated plaque build-up.

Depending on the structure of contemplated compounds, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM. Consequently, in vivo concentrations will generally be suitable to reduce BACE activity in vivo with respect to APP cleavage by at least 10%, and more typically by at least 25%.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. Furthermore, where the compound is formulated for intrathecal administration, it is generally preferred that the compound is prepared as an injectable solution, suspension, or emulsion. In still further contemplated formulations, contemplated compounds may be formulated for aerosol delivery (e.g., micropowderized, coated onto a dispersible carrier, dissolved in atomizable solvent, etc.)

It should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Additionally, it is contemplated that contemplated compounds may be combined (in vivo or in a pharmaceutical formulation or administration regimen) with another pharmaceutically active ingredient, and especially contemplated other ingredients include various drugs targeting amyloid plaque, tau hyperphosphorylation, various immunomodulatory drugs, and/or anti-inflammatory drugs (e.g., steroids and NSAIDS), etc. Concentrations of second pharmaceutically active ingredients are typically at or preferably below those recommended for stand-alone administration, however, higher concentrations are also deemed suitable for use herein.

Preferably, contemplated compounds will have an $IC_{50}$ (with respect to BACE inhibition and APP as substrate) of equal or less than 10 µM, more preferably of equal or less than 1 µM, and most preferably of equal or less than 100 nM, and will have no apparent toxicity at the $IC_{50}$ as measured above. Once candidate compounds (typically having $IC_{50}$ of equal or less than 1.0 µM, more typically equal or less than 0.1 µM, and most typically equal or less than 0.01 µM,) are identified, such compounds can be further modified to ascertain SAR and to produce compounds with higher potency, reduced toxicity, and/or increased bioavailability. Therefore, particularly preferred compounds not only include those as shown in Formulae I-XIII above, but also include those of Tables 1-4 below.

Experimental Data and Results
Synthetic Protocols:
Contemplated compounds can be prepared using various methods known in the art, and all of those are deemed suitable for use herein. Further particularly suitable methods will follow the generally synthetic protocol as described in US 2014/0371283 with slight modifications to accommodate various substituents.

Assay Systems to Evaluate APP Processing: Without being bound to a particular theory, it is believed that the active agent(s) described herein promote processing of APP by the nonamyloidogenic pathway and/or reduce or inhibit processing of APP by the amyloidogenic pathway. In the nonamyloidogeic pathway, APP is first cleaved by α-secretase within the Aβ sequence, releasing the APPsα ectodomain ("sAPPα"). In contrast, the amyloidogenic pathway is initiated when β-secretase cleaves APP at the amino terminus of the Aβ, thereby releasing the APPsβ ectodomain ("sAPPβ").

One method to evaluate the efficacy of the active agent(s) is to determine a reduction or elimination in the level of APP processing by the amyloidogenic pathway, e.g., a reduction or elimination in the level of APP processing by β-secretase cleavage in response to the administration of the agent(s) of interest. Assays for determining the extent of APP cleavage at the β-secretase cleavage site are well known in the art. Illustrative assays are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

ABBI Assay: APP Binding BACE Inhibitor (ABBI) activity of any of the compounds described herein can readily be verified using, for example, assays described herein. Basically, in certain embodiments a pair the assays are utilized to identify ABBI compounds that inhibit BACE cleavage of the MBP-C125 APP substrate, resulting in the inhibition of the production of C99 and the β-site peptide substrate (P5-P5') and also interacts with APP, for example, as measured by surface plasmon resonance (SPR) analysis.

In one illustrative embodiment, an MBP-C125 APP695 wt fusion protein can be used as one of the substrates and the second substrate can be the commercially available P5-P5' fluorescence substrate. Each of these substrates is incubated with recombinant BACE (R&D (cat #931-AS-050) in, for example, a 96 well plate format. For the MBP-C125 substrate the C-99 product from the BACE cleavage can be measured using an AlphaLisa assay as a readout. For the P5-5' substrate, the loss of fluorescence upon BACE cleavage can be used as the readout. For the SPR assay the binding analysis of contemplated compounds to fragments of the ectodomain of APP (eAPP) that are recombinantly prepared (see e.g., Libeu et al. (2012) PLoS ONE 7(6): e40027) would be done. An ABBI would inhibit the BACE cleavage of the MBP-C125 and/or the fluorescence substrate and would also bind to the ectodomain of APP such as the APP230-624 fragment.

Other Cell Free Assays: Illustrative assays that can be used to demonstrate the inhibitory activity of the active agent(s) are described, for example, in WO 2000/017369, WO 2000/0003819, and U.S. Pat. Nos. 5,942,400 and 5,744, 346. Such assays can be performed in cell-free incubations or in cellular incubations using cells expressing an alpha-secretase and/or beta-secretase and an APP substrate having a alpha-secretase and beta-secretase cleavage sites.

In further aspects of the inventive subject matter, contemplated compounds are contacted with an APP substrate containing alpha-secretase and beta-secretase cleavage sites of APP, for example, a complete APP or variant, an APP fragment, or a recombinant or synthetic APP substrate containing the amino acid sequence: KM-DA or NL-DA (APP-SW), is incubated in the presence of an alpha-secretase and/or beta-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. Agent(s) having the desired activity reduce or prevent cleavage of the APP substrate. Suitable substrates optionally include derivatives that may be fusion proteins or peptides that contain the substrate peptide and a modification useful to facilitate the purification or detection of the peptide or its alpha-secretase and/or beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nM to 10 µM substrate, approximately 10 to 200 pM enzyme, and approximately 0.1 nM to 10 µM of the agent(s), in aqueous solution, at an approximate pH of 4-7, at approximately 37° C., for a time period of approximately 10 minutes to 3 hours. These incubation conditions are illustrative only, and can be varied as required for the particular assay components and/or desired measurement system. Optimization of the incubation conditions for the particular assay components should account for the specific alpha-secretase and/or beta-secretase enzyme used and its pH optimum, any additional enzymes and/or markers that might be used in the assay, and the like. Such optimization is routine and will not require undue experimentation.

Another exemplary assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. This system can be used to screen for the inhibitory activity of the agent(s) of interest. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assays: Numerous cell-based assays can be used to evaluate the activity of agent(s) of interest on relative alpha-secretase activity to beta-secretase activity and/or processing of APP to release amyloidogenic versus non-amyloidogenic oligomers. Contact of an APP substrate with an alpha-secretase and/or beta-secretase enzyme within the cell and in the presence or absence of the agent(s) can be used to demonstrate alpha-secretase promoting and/or beta-secretase inhibitory activity of the agent(s). Preferably, the assay in the presence of the agent(s) provides at least about 30%, most preferably at least about 50% inhibition of the enzymatic activity, as compared with a non-inhibited control.

In one embodiment, cells that naturally express alpha-secretase and/or beta-secretase are used. Alternatively, cells are modified to express a recombinant alpha-secretase and/or beta-secretase or synthetic variant enzymes, as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the alpha-secretase and/or beta-secretase APP cleavage sites can be used, provided that the expressed APP is permitted to contact the enzyme and enzymatic cleavage activity can be analyzed.

Human cell lines that normally process $A\beta$ from APP provide a useful means to assay inhibitory activities of the agent(s). Production and release of $A\beta$ and/or other cleavage products into the culture medium can be measured, for example by immunoassay, such as Western blot or enzyme-linked immunoassay (EIA) such as by ELISA.

Cells expressing an APP substrate and an active alpha-secretase and/or beta-secretase can be incubated in the presence of the agents to demonstrate relative enzymatic activity of the alpha-secretase and/or beta-secretase as compared with a control. Relative activity of the alpha-secretase to the beta-secretase can be measured by analysis of one or more cleavage products of the APP substrate. For example, inhibition of beta-secretase activity against the substrate APP would be expected to decrease release of specific beta-secretase induced APP cleavage products such as $A\beta$ (e.g., $A\beta 40$ or $A\beta 42$), $sAPP\beta$ and APPneo. Promotion or enhancement of alpha-secretase activity against the substrate APP would be expected to increase release of specific alpha-secretase induced APP cleavage products such as $sAPP\alpha$ and p3 peptide.

Although both neural and non-neural cells process and release $A\beta$, levels of endogenous beta-secretase activity are low and often difficult to detect by EIA. The use of cell types known to have enhanced beta-secretase activity, enhanced processing of APP to $A\beta$, and/or enhanced production of $A\beta$ are therefore preferred. For example, transfection of cells with the Swedish Mutant form of APP (APP-SW); with the Indiana Mutant form (APP-IN); or with APP-SW-IN provides cells having enhanced beta-secretase activity and producing amounts of $A\beta$ that can be readily measured.

In such assays, for example, the cells expressing APP, alpha-secretase and/or beta-secretase are incubated in a culture medium under conditions suitable for alpha-secretase and/or beta-secretase enzymatic activity at its cleavage site on the APP substrate. On exposure of the cells to the agent(s), the amount of $A\beta$ released into the medium and/or the amount of CTF99 fragments of APP in the cell lysates is reduced as compared with the control. The cleavage products of APP can be analyzed, for example, by immune reactions with specific antibodies, as discussed above.

In certain embodiments, preferred cells for analysis of alpha-secretase and/or beta-secretase activity include primary human neuronal cells, primary transgenic animal neuronal cells where the transgene is APP, and other cells such as those of a stable 293 cell line expressing APP, for example, APP-SW.

In Vivo Assays—Animal Models: Various animal models can be used to analyze the activity of agent(s) of interest on relative alpha-secretase and/or beta-secretase activity and/or processing of APP to release Aβ. For example, transgenic animals expressing APP substrate, alpha-secretase and/or beta-secretase enzyme can be used to demonstrate inhibitory activity of the agent(s). Certain transgenic animal models have been described, for example, in U.S. Pat. Nos. 5,877,399; 5,612,486; 5,387,742; 5,720,936; 5,850,003; 5,877,015, and 5,811,633, and in Ganes et al. (1995) Nature 373:523. Preferred are animals that exhibit characteristics associated with the pathophysiology of AD. Administration of the agent(s) to the transgenic mice described herein provides an alternative method for demonstrating the inhibitory activity of the agent(s). Administration of the agent(s) in a pharmaceutically effective carrier and via an administrative route that reaches the target tissue in an appropriate therapeutic amount is also preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

On contacting an APP substrate with an alpha-secretase and/or beta-secretase enzyme in the presence of the agent(s) under conditions sufficient to permit enzymatic mediated cleavage of APP and/or release of Aβ from the substrate, desirable agent(s) are effective to reduce beta-secretase-mediated cleavage of APP at the beta-secretase cleavage site and/or effective to reduce released amounts of Aβ. The agent(s) are also preferably effective to enhance alpha-secretase-mediated cleavage of APP at the alpha-secretase cleavage site and to increase released amounts of sAPPα. Where such contacting is the administration of the agent(s) to an animal model, for example, as described above, the agent(s) is effective to reduce Aβ deposition in brain tissues of the animal, and to reduce the number and/or size of beta amyloid plaques. Where such administration is to a human subject, the agent(s) is effective to inhibit or slow the progression of disease characterized by enhanced amounts of Aβ, to slow the progression of AD in the, and/or to prevent onset or development of AD in a patient at risk for the disease.

Using the experimental conditions and parameters as described above, the inventors investigated the effects of contemplated compounds on BACE activity with respect to $IC_{50}$ values, preference towards APP, and various pharmacokinetic parameters in various in vitro and in vivo experiments. Most notably, many of the compounds had submicromolar $IC_{50}$ values, exhibited pronounced preference towards APP in BACE inhibition, and were able to cross the blood brain barrier in pharmacologically meaningful quantities. Table 1 and Table 2 below list exemplarily results for selected compounds presented herein.

TABLE 1

| FAH # | Structure | MW | cLogP | Primary BACE1 IC50 |
|---|---|---|---|---|
| 3 | 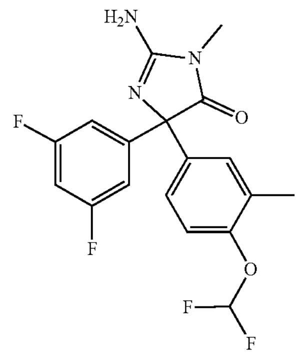 [SMILES: Cc1cc(C2(c3cc(F)cc(F)c3)N=C(N)N(C)C2=O)ccc1OC(F)F] | 381.3 | 3.34 | 0.53 μM |
| 17 | 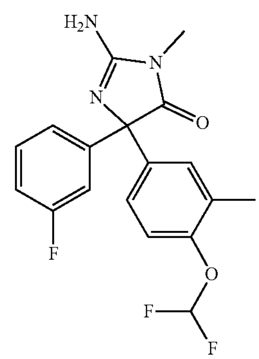 [SMILES: Cc1cc(C2(c3cccc(F)c3)N=C(N)N(C)C2=O)ccc1OC(F)F] | 363.33 | 3.2 | 0.15 |
| 22 | 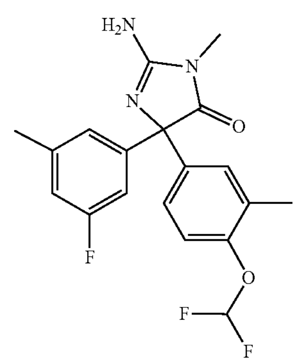 | 377.36 | 3.62 | 0.71 |
| 23 | 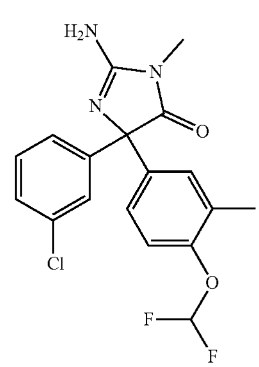 [SMILES: Cc1cc(C2(c3cccc(Cl)c3)N=C(N)N(C)C2=O)ccc1OC(F)F] | 379.79 | 3.74 | 0.32 |

TABLE 1-continued

| # | Structure | MW | cLogP | Primary BACE1 IC50 |
|---|---|---|---|---|
| 25 | (structure: 2-amino-3-methyl-5-(3-fluoro-5-chlorophenyl)-5-(3-methyl-4-(difluoromethoxy)phenyl)imidazol-4-one) | 397.78 | 3.85 | 0.57 |
| 27 | (structure: 2-amino-3-methyl-5-(m-tolyl)-5-(3-methyl-4-(difluoromethoxy)phenyl)imidazol-4-one) | 359.37 | 3.51 | 0.13 |
| 28 | (structure: 2-amino-3-methyl-5-(3-(trifluoromethyl)phenyl)-5-(3-methyl-4-(difluoromethoxy)phenyl)imidazol-4-one) | 413.34 | 3.96 | 0.38 |
| 30 HCl | (structure: 2-amino-3-methyl-5-(1-methyl-1H-pyrazol-4-yl)-5-(3-methyl-4-(difluoromethoxy)phenyl)imidazol-4-one HCl) | 385.8 | 2.0 | |
| 31 | (structure: 2-amino-3-methyl-5-(3-fluorophenyl)-5-(3-methyl-4-(1-fluoroethoxy)phenyl)imidazol-4-one) | 379.4 | 3.41 | 4.0 |
| 32 | (structure: 2-amino-3-methyl-5-(3-(pyridin-3-yl)phenyl)-5-(3-methyl-4-(difluoromethoxy)phenyl)imidazol-4-one) | 422.4 | 3.78 | 0.07 |

| FAH # | sAPPalpha | sAPPbeta | sAPP (α/β) | Abeta 1-42 | sAPPα/ A=62 | APP Kd |
|---|---|---|---|---|---|---|
| 3 | ↑>10% | ↓>20% | ↑≈50% | ↓>20% | ↑>50% | ≈0.3 μM |
| 17 | ↑>20% | ↓>30% | ↑>100% | ↓>30% | ↑>100% | + |
| 22 | ↑>10% | ↓>20% | ↑≈50% | ↓>25% | ↑>100% | TBA |
| 23 | ↑>20% | ↓>20% | ↑>50% | ↓>25% | ↑>100% | TBA |
| 25 | ↑>10% | ↓>20% | ↑≈50% | ↓>20% | ↑>40% | TBA |
| 27 | ↑>30% | ↓>30% | ↑>100% | ↓>40% | ↑>100% | TBA |
| 28 | ↑>20% | ↓>20% | ↑>50% | ↓>20% | ↑>40% | TBA |
| 30 HCl | ↑>10% | ↓>20% | ↑≈40% | | | |
| 31 | Unchanged | ↓>30% | ↑>100% | ↓>30% | ↑>50% | |
| 32 | ↑>20% | ↓>30% | ↑>100% | ↓>60% | ↑>100% | |

TABLE 1

| FAH # | Structure | MW | cLogP | Primary BACE1 IC50 |
|---|---|---|---|---|
| 33 | (structure: 2-amino-3-methyl-5-(pyrimidin-5-yl)-5-(3-methyl-4-(difluoromethoxy)phenyl)imidazol-4-one) | 347.32 | 0.98 | 10.00 |

TABLE 1-continued
| | | | | |
|---|---|---|---|---|
| 37 | 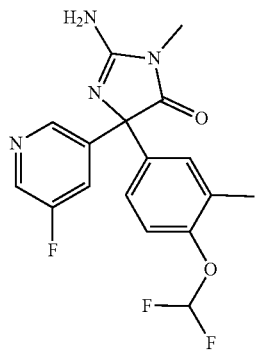 | 364.33 | 2.16 | 0.15 |
| 38 | 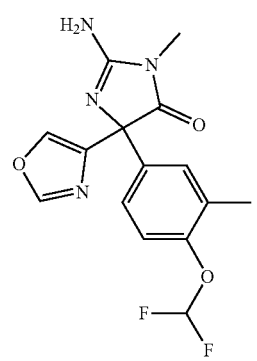 [SMILES: Cc1cc(C2(c3cocn3)N=C(N)N(C)C2=O)ccc1OC(F)F] | 336.3 | 1.61 | >10 |
| 42 | 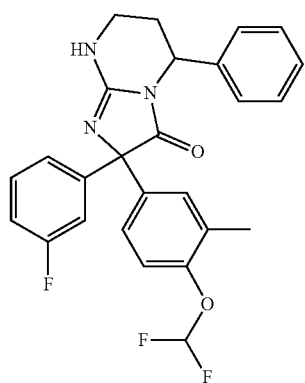 [SMILES: Cc1cc(C2(c3cccc(F)c3)N=C3NCCC(c4ccccc4)N3C2=O)ccc1OC(F)F] | 439.44 | 4.62 | 2.3 |
| 44 | 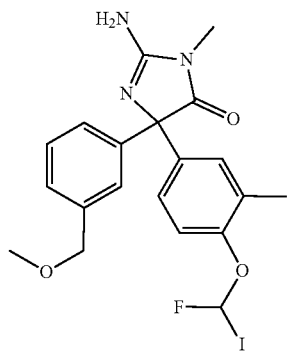 | 389.4 | 3.01 | 0.3 |
| 46 | 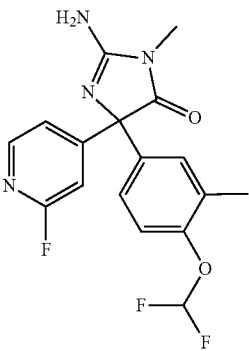 [SMILES: Cc1cc(C2(c3ccnc(F)c3)N=C(N)N(C)C2=O)ccc1OC(F)F] | 364.33 | 2.3 | 1.2 |
| 47 | 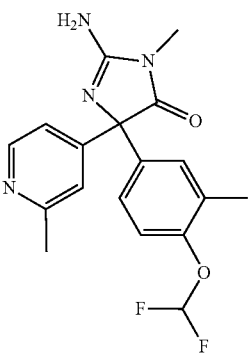 [SMILES: Cc1cc(C2(c3ccc(OC(F)F)c(C)c3)N=C(N)N(C)C2=O)ccn1] | 360.13 | 2.23 | 1.4 |
| 48 | 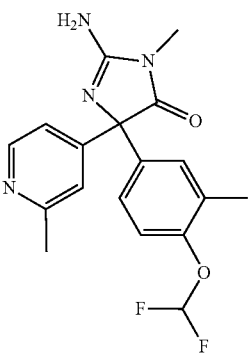 [SMILES: Cc1cc(C2(c3ccc(OC(F)F)c(C)c3)N=C(N)N(C)C2=O)ccn1] | 376.36 | 2.19 | 4.8 |
| 53 | 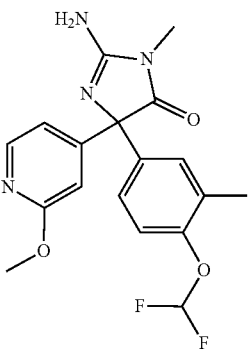 | 390.4 | 2.21 | 2.0 |

TABLE 1-continued

| 59 | H₂N structure | 397.42 | 2.41 | 1.5 |
| 62 | H₂N structure | 480.86 | 2.62 | 0.06 |

| FAH # | sAPPalpha | sAPPbeta | sAPP (α/β) | Abeta 1-42 | sAPPα/Aβ | APP Kd |
|---|---|---|---|---|---|---|
| | | | Secondary (1st test, n = 3) | | | |
| 33 | ↑>10% | Unchanged | ↑≈10% | ↓≈10% | ↑>20% | |
| 37 | ↑>10% | ↓>20% | ↑>50% | ↓≈20% | ↓>40% | |

TABLE 1-continued

| | | | | | |
|---|---|---|---|---|---|
| 38 | | | unchanged | | |
| 42 | ↑>10% | ↓>30% | ↑>50% | ↓≈10% | unchanged |
| 44 | ↑>10% | ↓>30% | ↑>100% | ↓>30% | ↓>100% |
| 46 | ↑>10% | ↓<10% | ↑≈10% | ↓>20% | ↓>40% |
| 47 | ↑>10% | ↓>20% | ↑>50% | ↓≈10% | ↓>20% |
| 48 | ↑>10% | ↓>20% | ↑≈50% | ↓≈10% | ↓>20% |
| 53 | ↑>10% | ↓<10% | ↑≈50% | ↓<10% | ↓≈20% |
| 59 | | | Toxic | | |
| 62 | ↑>10% | ↓>20% | ↑≈50% | ↓<10% | ↓≈30% |

Figure 1B:
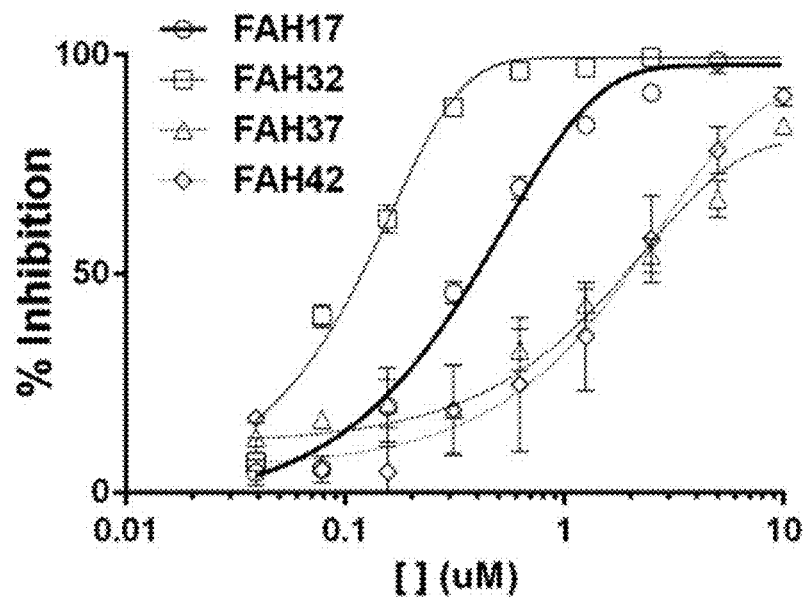
FIGS. 1B-1D depict exemplary test results for selected compounds.
Figure 1C:
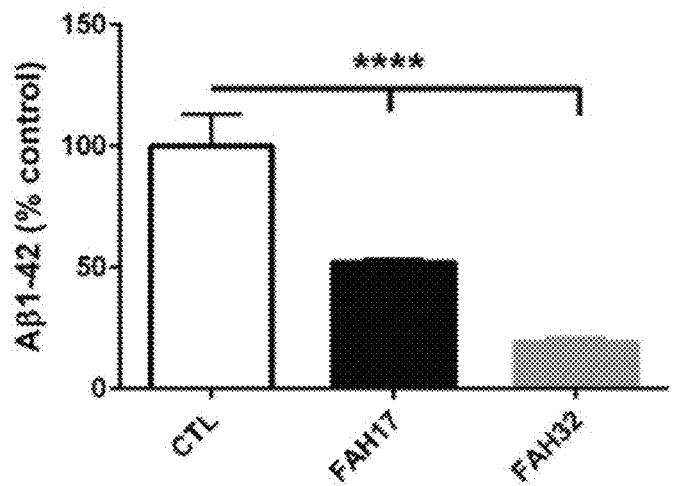
Figure 1D:
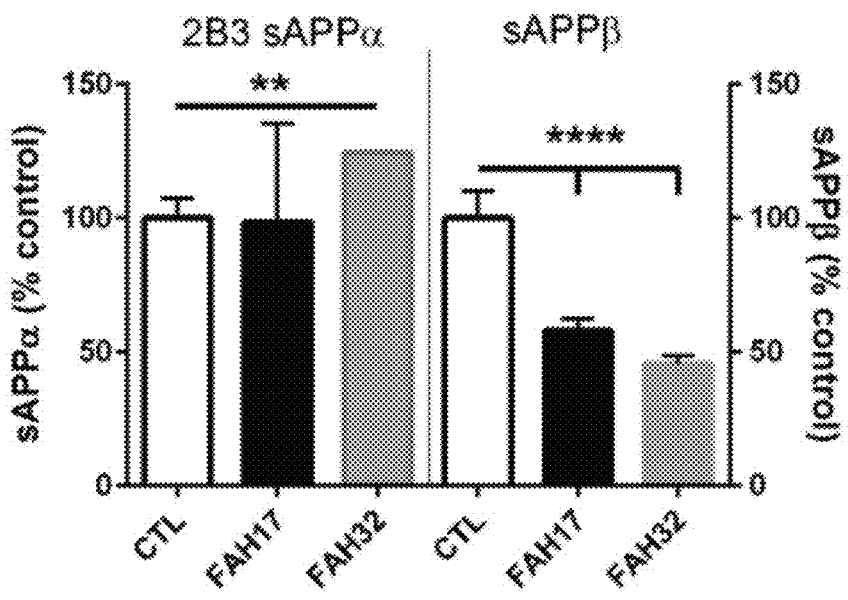
Figure 2A:
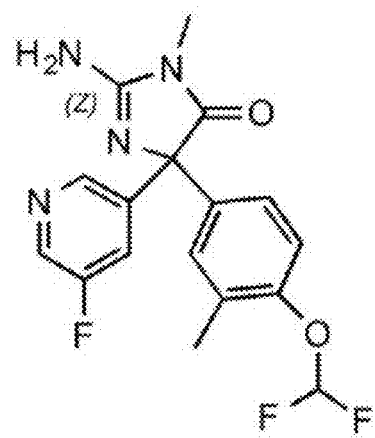
FIG. 2A depicts an exemplary compound according to the inventive subject matter.

More particularly, FIG. 1A shows the structures for FAH17 and FAH32, which were tested in an in vitro BACE inhibition assay along with two other compounds, FAH37 and FAH42 (for structures, see FIG. 2A and Table 2, respectively). As can be readily seen from FIG. 1B, FAH32 had significantly reduced $IC_{50}$ in the BACE assay. When tested with CHO-7W cells that were stably transfected with human APP (wildtype), Aβ1-42 peptide formation was substantially reduced using FAH32 versus control and FAH17 as shown in FIG. 1C. On the other hand, FAH32 increased sAPPα formation as compared to FAH17, indicating a higher selectivity of FAH32 towards APP, while sAPPβ formation was reduced as compared to FAH17 as can be seen from FIG. 1D.

Figure 2B:
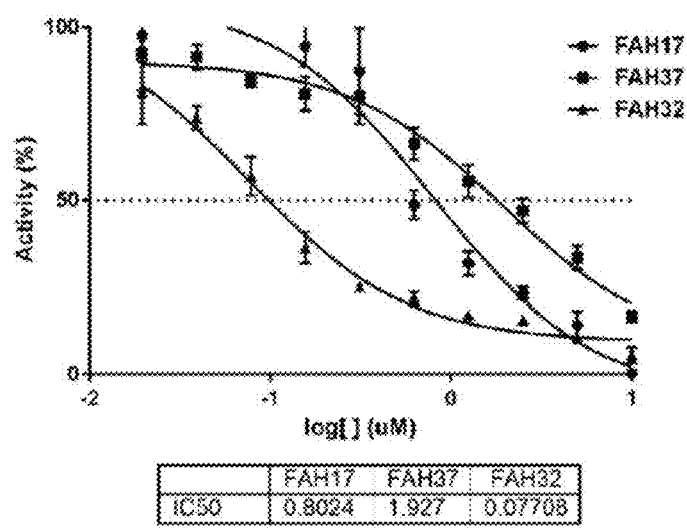
FIGS. 2B-2C depict exemplary test results for selected compounds.
Figure 2C:
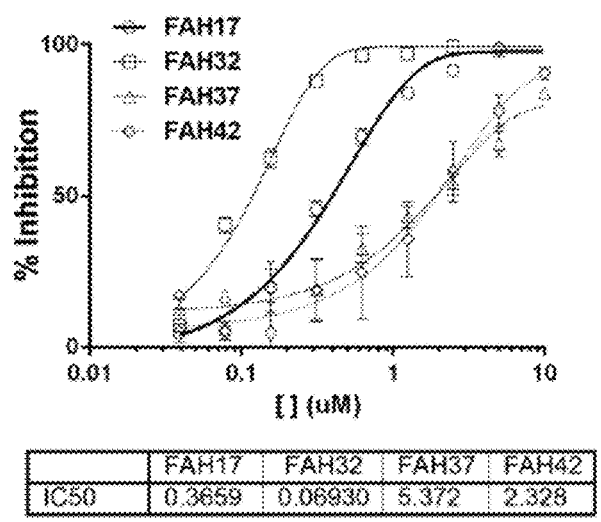
Figure 3A:
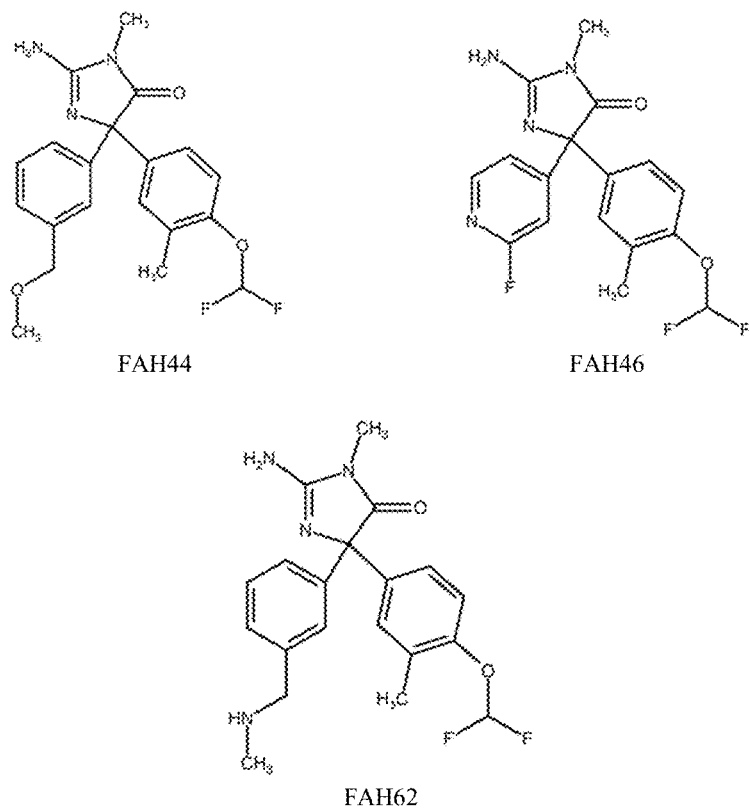
FIG. 3A depicts exemplary compounds according to the inventive subject matter.
Figure 3B:
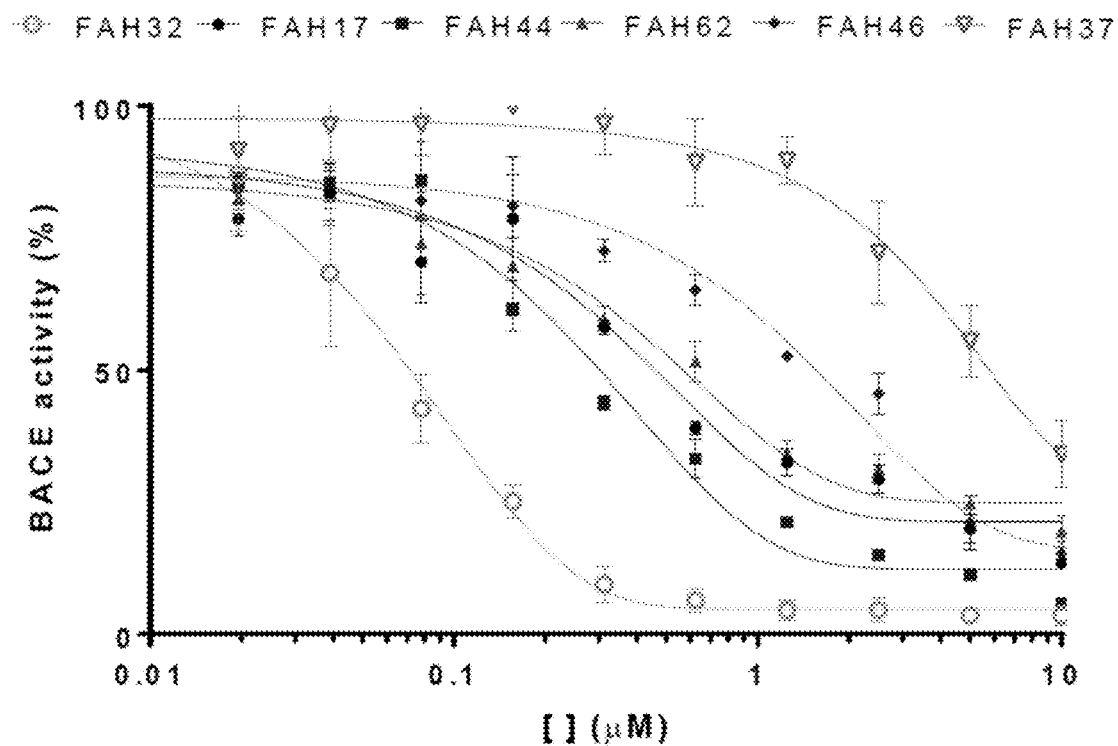
FIGS. 3B-3E depict exemplary test results for selected compounds.
Figure 3C:
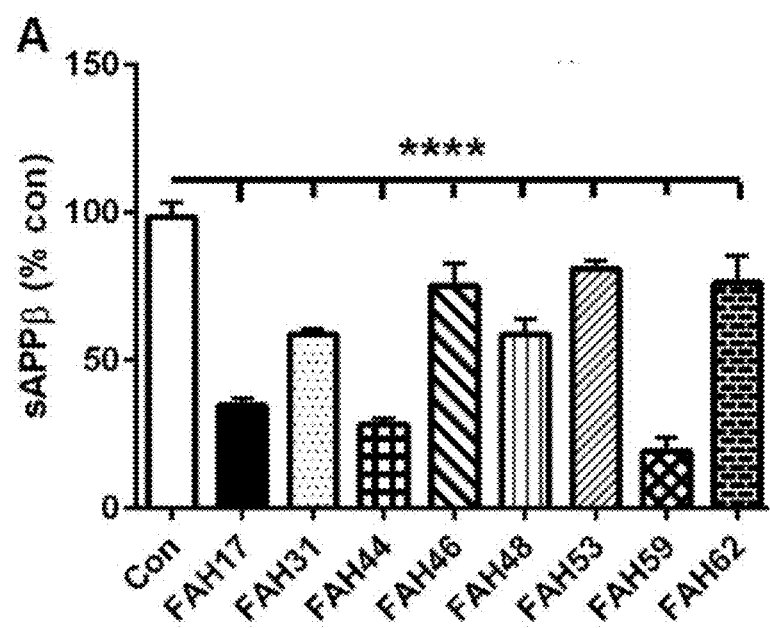
Figure 3D:
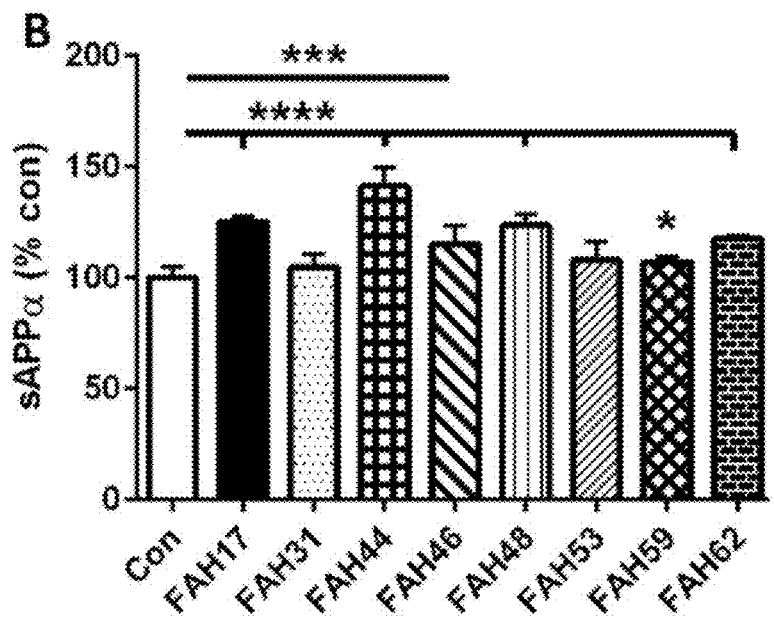
Figure 3E:
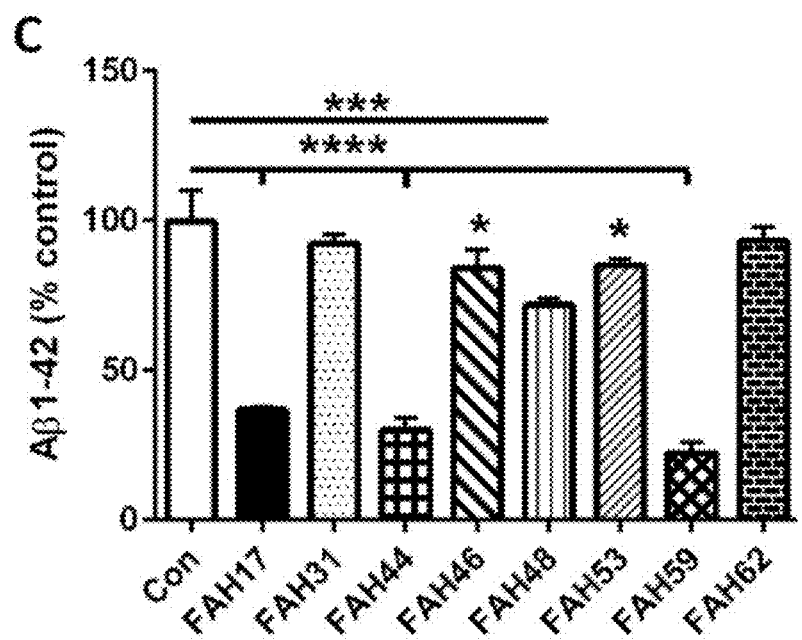

When compared with FAH37 as shown in FIG. 2A, FAH37 was less effective in reducing BACE activity in vitro as shown in FIG. 2B, and similar differences in inhibition were also evident from a P5-P5' fluorescence assay in vitro as is shown in FIG. 2C. Further compounds were evaluated and selected compounds are shown in FIG. 3A with test results for a BACE activity assay shown in FIG. 3B. Notably, even relatively moderate changes in structure resulted in substantial differences in observed BACE activity. These compounds were further tested for selectivity or preference towards APP in a cell based model, and the results are shown for sAPPβ production in FIG. 3C, for sAPPα in FIG. 3D, and for Aβ1-42 production in FIG. 3E.

TABLE 3 exemplarily shows further physical and pharmacokinetic data for selected compounds according to the inventive subject matter.

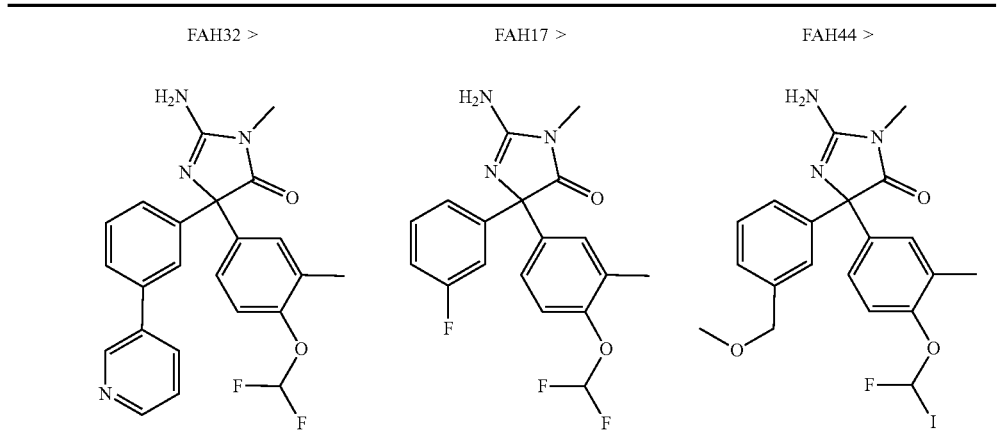

| | FAH32 > | FAH17 > | FAH44 > |
|---|---|---|---|
| $IC_{50}$ | ~0.06 µM | ~0.1 µM | ~0.25 µM |
| MW | 422 | 363 | 389 |
| Sol | Med | Med | Excellent |
| $C_{max}$ brain | <0.02 µM | ~0.3 µM | ~0.2 µM |

TABLE 3-continued exemplarily shows further physical and pharmacokinetic data for selected
compounds according to the inventive subject matter.

| | FAH62 > | FAH46 >> | FAH37 |
|---|---|---|---|
| |  | 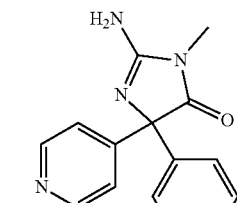 | 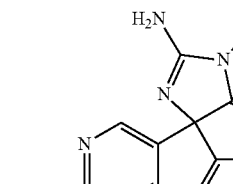 |
| $IC_{50}$ | ~0.6 μM | ~1.2 μM | ~5.3 μM |
| MW | 388 | 364 | 364 |
| Sol | Good | Good | Good |
| $C_{max}$ brain | Underway | ~0.3 μM | ~0.11 uM |

Figure 4:
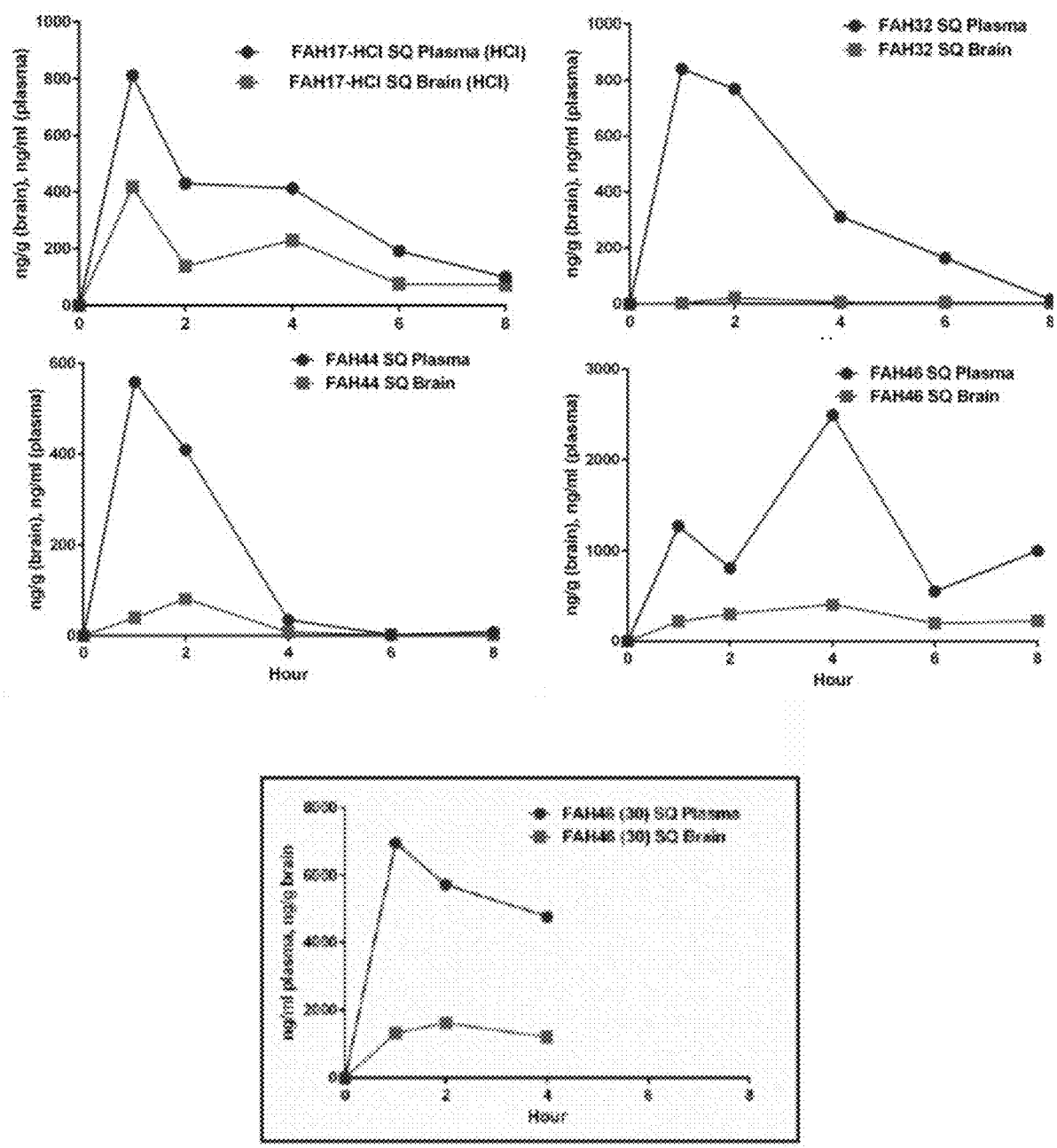
FIG. 4 depicts exemplary pharmacokinetic test results for selected compounds.
Figure 5A:
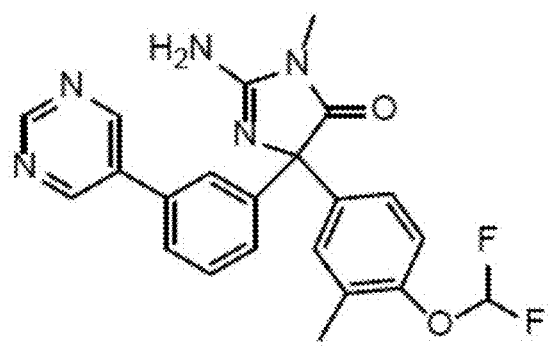
FIG. 5A depicts an exemplary compound according to the inventive subject matter.
Figure 5B:
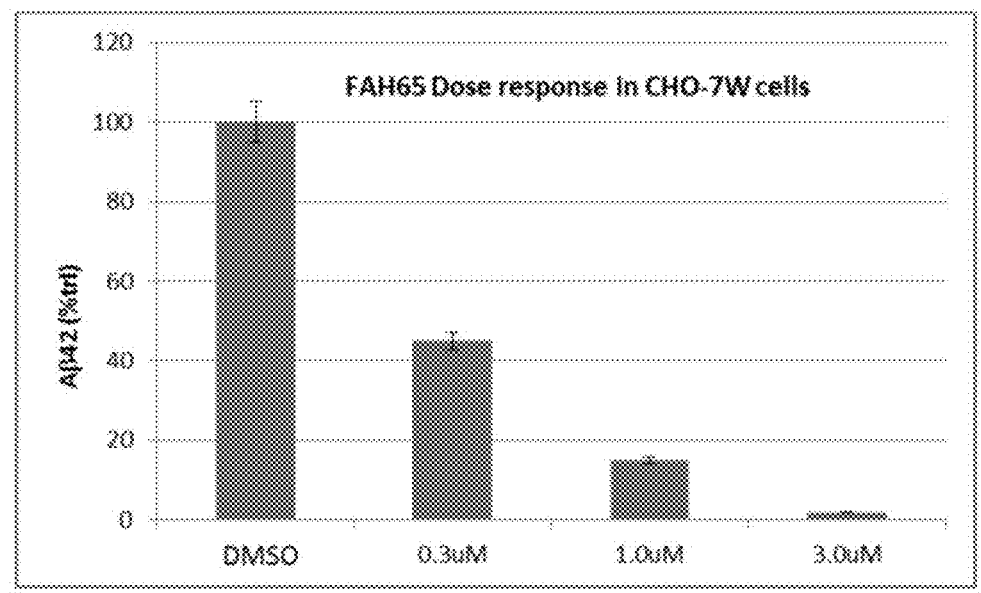
FIGS. 5B-5C depict exemplary test results for the compound of FIG. 5A.
Figure 5C:
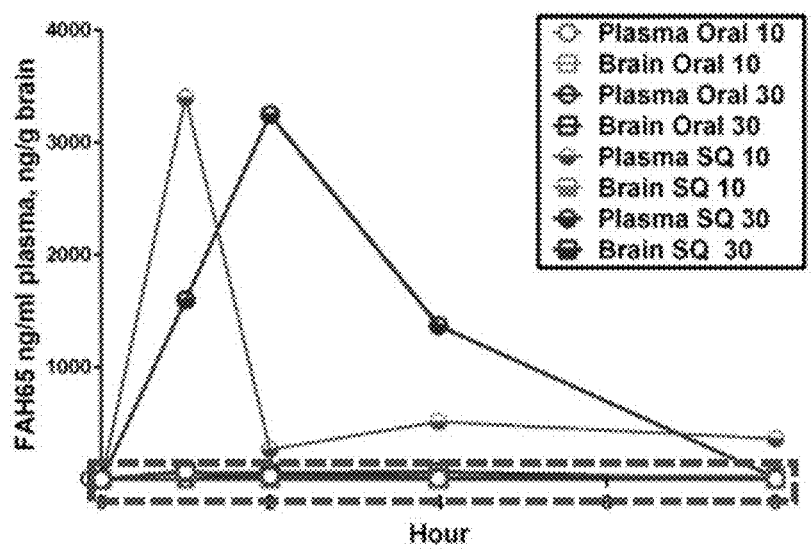
Figure 5C:
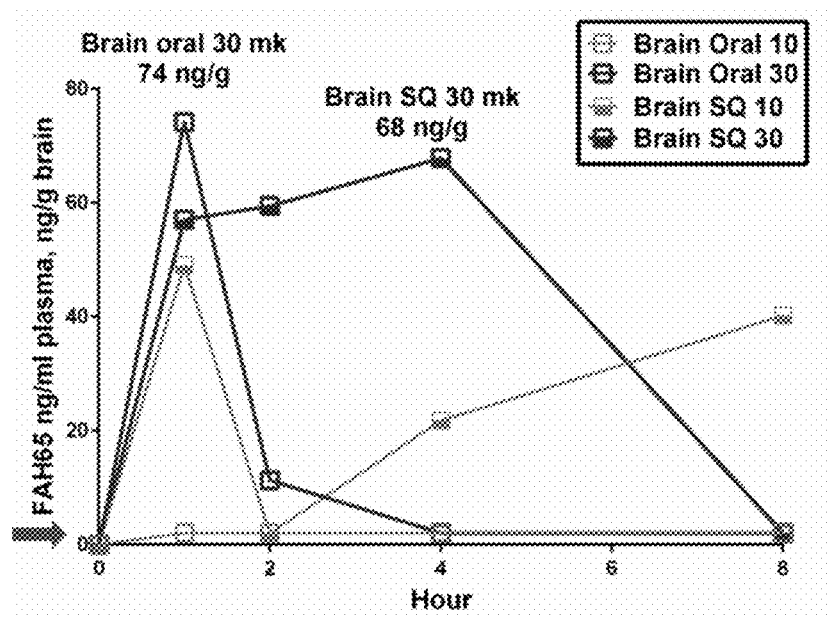
Figure 6A:
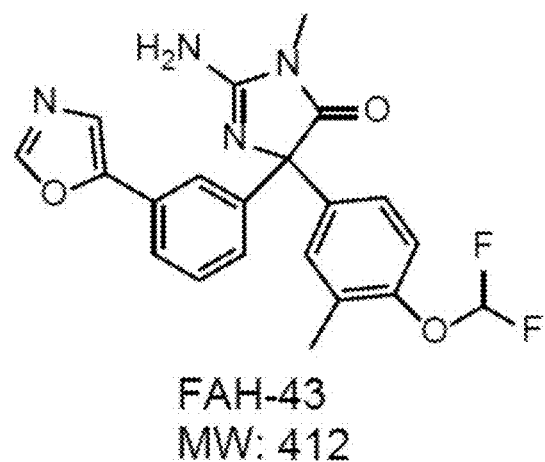
FIG. 6A depicts an exemplary compound according to the inventive subject matter.
Figure 6B:
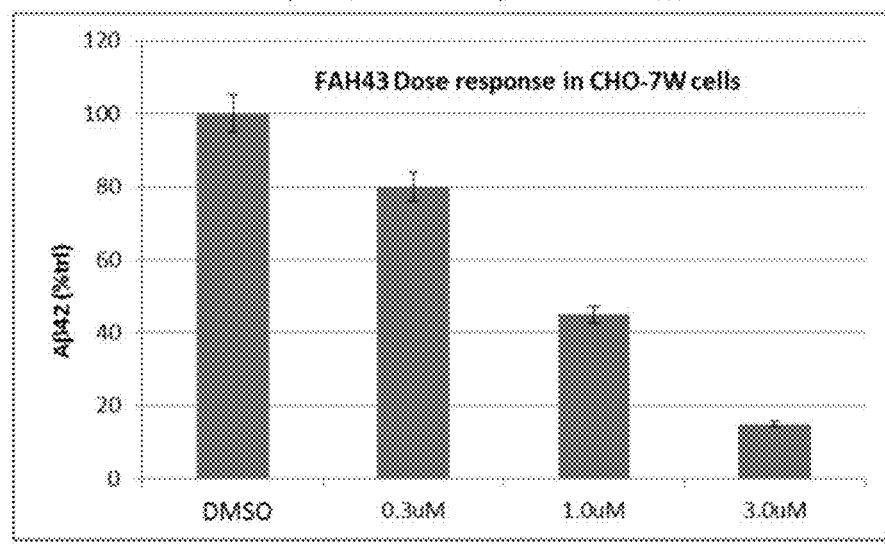
FIG. 6B depicts exemplary test results for the compound of FIG. 6A.
Figure 7A:
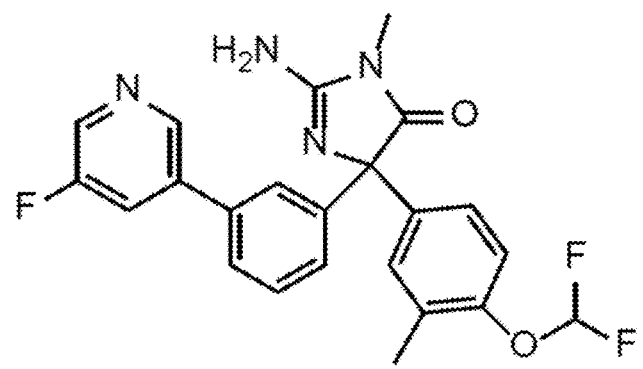
FIG. 7A depicts an exemplary compound according to the inventive subject matter.
Figure 7B:
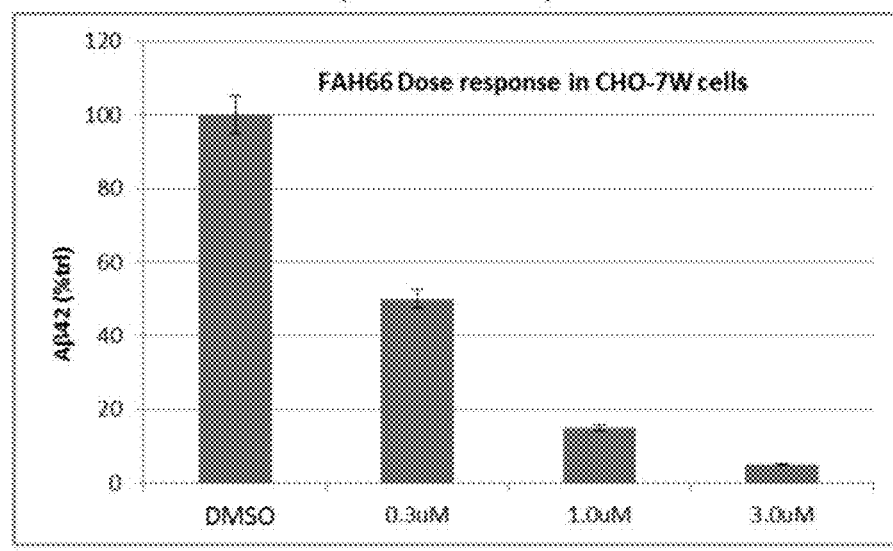
FIG. 7B depicts exemplary test results for the compound of FIG. 7A.
Figure 8:
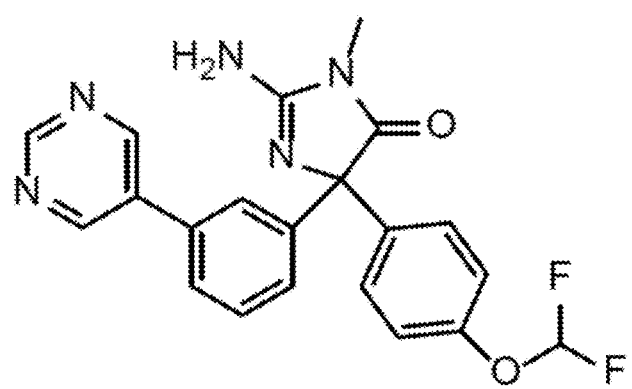
FIG. 8 depicts an exemplary compound according to the inventive subject matter and an exemplary test results for the exemplary compound.

Pharmacokinetic data for selected compounds of Table 3 are shown in FIG. 4. As is readily apparent, not all compounds were equally able to cross the blood brain barrier, but most compounds did reach pharmacologically meaningful levels given their low $IC_{50}$ values. FIG. 5A provides a further exemplary compound (FAH65) and FIG. 5B depicts dose response data for Aβ1-42 production in a cell based system.. Further shown are effects observed with regard to Aβ1-42 production, sAPPβ and sAPPα formation. As can be seen, FAH65 exhibits clear preference towards APP in BACE inhibition, and strongly reduces Aβ1-42 production. Moreover, FAH65 has also desirable pharmacological properties as can be seen from FIG. 5C. Here, data are presented for oral and subcutaneous administration (SQ) at dosages of 10- and 30 mg/kg. Values are measured in plasma and brain, and the lower graph shows a magnified scale of the area in the box in the upper graph of FIG. 5C. Given the low $IC_{50}$ value of the compound, it should be appreciated that pharmaceutically meaningful concentrations can be achieved in the brain. Similar results for the compounds of FIGS. 6A and 7A are presented in FIGS. 6B and 7B. Once more, it should be noted that these exemplary compounds are preferential towards APP in BACE inhibition as can be taken from the data for Aβ1-42, sAPPβ, and sAPPα formation. Similar data are expected for FAH74 as shown in FIG. 8, which had a $IC_{50}$ of 9 nM as determined by an in vitro BACE inhibition assay.

Additional compounds according to the inventive subject matter and associated data are shown in Table 4 below in which MW indicates molecular weight, cLogP is the partition coefficient (log ($c_{octane}/c_{water}$)), TPSA is total polar surface area, BACE $IC_{50}$ is in micromolar, and PAMPA is parallel artificial membrane premeability assay.

| Name | Struture | MW | cLogP | TPSA | BACE1 IC50 (μM) | PAMPA |
|---|---|---|---|---|---|---|
| FAH-01 | | 301.30 | 1.63 | 58.69 | 2.67<br>4.7 | 2.33 |

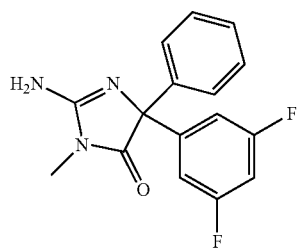 [SMILES: CN1C(=O)C(c2ccccc2)(c2cc(F)cc(F)c2)N=C1N]

-continued

| Name | Struture | MW | cLogP | TPSA | BACE1 IC50 (μM) | PAMPA |
|---|---|---|---|---|---|---|
| FAH-02 | | 367.30 | 1.80 | 67.92 | 2.13<br>9.2 | 1.51 |
| FAH-03 | | 381.33 | 2.15 | 67.92 | 0.53<br>4.5<br>5.7 | 1.91 |
| FAH-04 | | 362.30 | 1.80 | 67.92 | 2.23<br>3.5 | 1.38 |
| FAH-05 | | 329.35 | 2.32 | 58.69 | 6.46 | |
| FAH-06 | | 345.35 | 1.93 | 67.09 | 0.6<br>4.1 | 2.45 |

-continued

| Name | Struture | MW | cLogP | TPSA | BACE1 IC50 (μM) | PAMPA |
|------|----------|----|----|------|------|-------|
| FAH-07 | | 316.31 | 1.03 | 71.58 | | |
| FAH-08 | | 345.35 | 1.91 | 67.92 | 2.30 | |
| FAH-09 | | 359.38 | 2.25 | 67.92 | 1.40 | |
| FAH-10 | | 333.31 | 2.08 | 58.69 | 1.60 | |
| FAH-11 | | 332.31 | 2.89 | 80.81 | 1.80 | |

-continued

| Name | Struture | MW | cLogP | TPSA | BACE1 IC50 (μM) | PAMPA |
|---|---|---|---|---|---|---|
| FAH-12 | | 349.31 | 1.66 | 67.92 | 2.60 | |
| FAH-13 | | 370.28 | 1.54 | 71.58 | | |
| FAH-14 | | 337.23 | 1.84 | 58.69 | 1.50 | |
| FAH-15 | | 320.27 | 1.08 | 71.58 | 2.00 | |
| FAH-16 | | 303.27 | −0.20 | 84.47 | | |

-continued

| Name | Struture | MW | cLogP | TPSA | BACE1 IC50 (μM) | PAMPA |
|---|---|---|---|---|---|---|
| FAH-17 | | 363.34 | 2.05 | 67.92 | 0.15/0.09<br>0.37<br>0.78<br>1.3<br>0.82 | 1.90 |
| FAH-18 | | 345.35 | 1.93 | 67.92 | 0.18<br>0.24 | |
| FAH-19 | | 399.32 | 2.25 | 67.92 | 0.96 | |
| FAH-20 | | 405.42 | 3.23 | 67.92 | | |
| FAH-21 | | 395.36 | 2.49 | 67.92 | | |

-continued

| Name | Struture | MW | cLogP | TPSA | BACE1 IC50 (μM) | PAMPA |
|---|---|---|---|---|---|---|
| FAH-22 | | 377.37 | 2.39 | 67.92 | 0.71 | |
| FAH-23 | | 379.79 | 2.55 | 67.92 | 0.32 | |
| FAH-24 | | 336.30 | 1.61 | 93.95 | | |
| FAH-25 | | 397.78 | 2.65 | 67.92 | 0.57 | |
| FAH-26 | | 369.37 | 1.91 | 96.16 | | |
| FAH-27 | | 359.38 | 2.29 | 67.92 | 0.13 | |

-continued

| Name | Struture | MW | cLogP | TPSA | BACE1 IC50 (μM) | PAMPA |
|---|---|---|---|---|---|---|
| FAH-28 | | 413.35 | 2.79 | 67.92 | 0.38 | |
| FAH-29 | | 387.43 433.46 | 3.13 | 67.92 | 11 | 4.01 |
| FAH-30 | | 349.34 | 1.46 | 85.74 | 2.00 | |
| FAH-31 | | 379.41 | 2.27 | 82.94 | 3.96 | 3.07 |
| FAH-32 | | 422.43 | 3.78 | 80.81 | 0.07 0.05 | 0.91 |
| FAH-33 | | 347.32 393.34 | 0.98 | 93.70 | 10 | |

-continued

| Name | Struture | MW | cLogP | TPSA | BACE1 IC50 (μM) | PAMPA |
|---|---|---|---|---|---|---|
| FAH-34 | | 352.36 | 0.80 | 108.05 | | |
| FAH-35 | | 388.37 | 1.03 | 111.01 | | |
| FAH-36 | | 429.40 | 1.68 | 86.60 | | |
| FAH-37 | | 364.33 | 2.16 | 80.81 | 1.93<br>2.8<br>5.3<br>4.7 | 0.54 |
| FAH-38 | | 336.30<br>382.32 | 1.61 | 93.95 | 15.26 | |
| FAH-39 | | 360.36 | 1.54 | 80.81 | | |
| FAH-40 | | 383.40 | 2.97 | 67.92 | | |

-continued

| Name | Struture | MW | cLogP | TPSA | BACE1 IC50 (μM) | PAMPA |
|---|---|---|---|---|---|---|
| FAH-41 | | 369.37 | 2.05 | 67.92 | | |
| FAH-42 | | 439.44 | 3.46 | 67.92 | 2.3<br>2.7 | 2.29 |
| FAH-43 | | 412.40 | 2.21 | 95.56 | 0.14 | 0.79 |
| FAH-44 | | 389.40 | 3.01 | 77.15 | 0.3<br>0.05 | 0.91 |
| FAH-45 | | 380.36 | 0.23 | 104.79 | | |
| FAH-46 | | 364.33 | 2.30 | 82.42 | 1.6 | 0.65 |

-continued

| Name | Struture | MW | cLogP | TPSA | BACE1 IC50 (μM) | PAMPA |
|---|---|---|---|---|---|---|
| FAH-47 | | 360.36 | 2.23 | 82.42 | 1.4 | 0.46 |
| FAM-48 | | 376.36 | 2.19 | 91.65 | 4.80 | 0.68 |
| FAH-49 | | 414.34 | 1.79 | 82.42 | | |
| FAH-50 | | 388.42 | 2.13 | 82.42 | | |
| FAH-51 | | 389.41 | 1.13 | 85.66 | | |
| FAH-52 | | 389.41 | 0.78 | 85.66 | | |

-continued

| Name | Struture | MW | cLogP | TPSA | BACE1 IC50 (μM) | PAMPA |
|---|---|---|---|---|---|---|
| FAH-53 | | 390.39 | 2.21 | 91.65 | 1.90 | 0.26 |
| FAH-54 | | 391.38 | 0.10 | 104.54 | | |
| FAH-55 | | 380.78 | 2.59 | 82.42 | | |
| FAH-56 | | 377.36 | 0.68 | 104.54 | | |
| FAH-57 | | 384.39 | 2.83 | 82.42 | 0.24 ? | 0.61 |
| FAH-58 | | 364.33 | 1.04 | 82.42 | | |
| FAH-59 | | 351.39 397.42 | 2.41 | 67.92 | 1.5 0.75 | 4.43 |

| Name | Struture | MW | cLogP | TPSA | BACE1 IC50 (μM) | PAMPA |
|---|---|---|---|---|---|---|
| FAH-60 | | 423.42 | 2.62 | 93.71 | | |
| FAH-61 | | 389.0 | 1.81 | 92.82 | | |
| FAH-62 | | 388.41 480.46 | 2.62 | 79.96 | 0.37 | 0.35 |
| FAH-63 | | 402.22 494.49 | 3.02 | 79.96 | 1.18 | 0.38 |
| FAH-64 | | 400.42 492.48 | 3.15 | 79.96 | 3.20 | 0.35 |
| FAH-65 | | 423.42 | 3.08 | 98.71 | 0.015 0.06 0.04 0.0032 | 0.44 |

-continued

| Name | Struture | MW | cLogP | TPSA | BACE1 IC50 (μM) | PAMPA |
|---|---|---|---|---|---|---|
| FAH-66 | | 440.42 | 4.09 | 80.82 | 0.018<br>0.12 | 1.15 |
| FAH-67<br>NANT-S039 | | 366.41 | 2.29 | 71.17 | 24.25 | 0.20 |
| FAH-68<br>NANT-S056 | | 408.49 | 3.72 | 71.17 | 16.10 | 0.20 |
| FAH-69<br>(V420) | | 432.47 | 3.54 | 98.96 | | |
| FAH-70 | | 389.40 | 1.97 | 93.71 | | |

-continued

| Name | Struture | MW | cLogP | TPSA | BACE1 IC50 (μM) | PAMPA |
|---|---|---|---|---|---|---|
| FAH-71 | | 404.37 | 0.20 | 122.81 | | |
| FAH-72 | | 423.42 | 2.62 | 83.71 | | |
| FAH-73 | | 421.44 | 4.86 | 67.93 | 0.87 | |
| FAH-74 | | 409.40 | 2.70 | 93.71 | 0.01 | |
| FAH-75 | | 357.42 | 2.51 | 84.48 | | |

-continued
| Name | Struture | MW | cLogP | TPSA | BACE1 IC50 (μM) | PAMPA |
|---|---|---|---|---|---|---|
| FAH-76 V-445 | 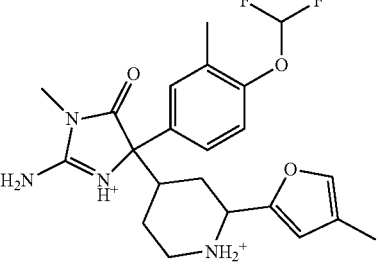 | 432.49 | 3.26 | 93.10 | | |
| FAH-77 V-446 | 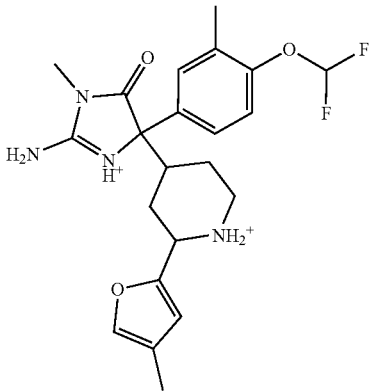 [SMILES: Cc1coc(C2CC(C3(c4ccc(OC(F)F)c(C)c4)[NH+]=C(N)N(C)C3=O)CC[NH2+]2)c1] | 446.51 | 3.64 | 93.10 | | |
| FAH-78 NANT-S037 | 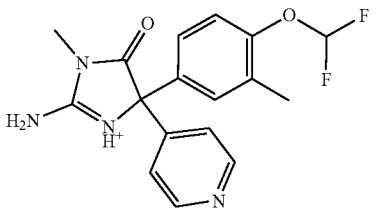 [SMILES: Cc1cc(C2(c3ccncc3)[NH+]=C(N)N(C)C2=O)ccc1OC(F)F] | 346.34 | 1.79 | 80.82 | 2.73 | 0.45 |
| FAH-79 NANT-S038 | 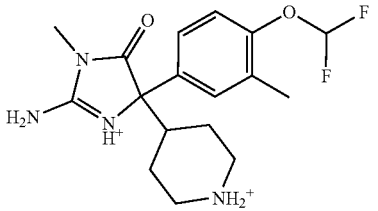 [SMILES: Cc1cc(C2(C3CC[NH2+]CC3)[NH+]=C(N)N(C)C2=O)ccc1OC(F)F] | 352.40 | 1.70 | 79.96 | 17.65 | 0.32 |
| FAH-80 NANT-S044 | 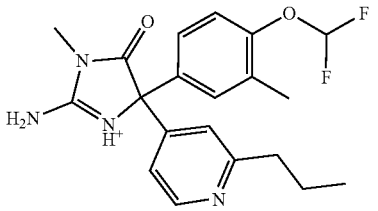 [SMILES: CCCc1cc(C2(c3ccc(OC(F)F)c(C)c3)[NH+]=C(N)N(C)C2=O)ccn1] | 388.48 | 3.31 | 80.82 | 1.67 | 0.73 |
| FAH-81 NANT-S045 | 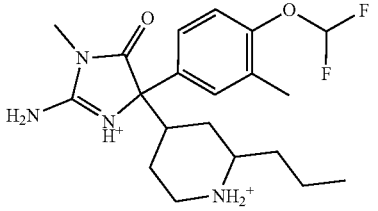 [SMILES: CCCC1CC(C2(c3ccc(OC(F)F)c(C)c3)[NH+]=C(N)N(C)C2=O)CC[NH2+]1] | 394.48 | 3.47 | 79.96 | 14.88 | 0.30 |

-continued

| Name | Struture | MW | cLogP | TPSA | BACE1 IC50 (µM) | PAMPA |
|---|---|---|---|---|---|---|
| FAH-82 V-454 | 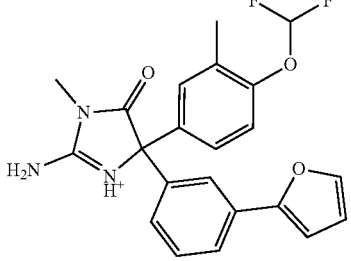 | 412.42 | 2.89 | 81.05 | | |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A compound having a structure according to any one of Formula IV-Formula X:

Formula IV
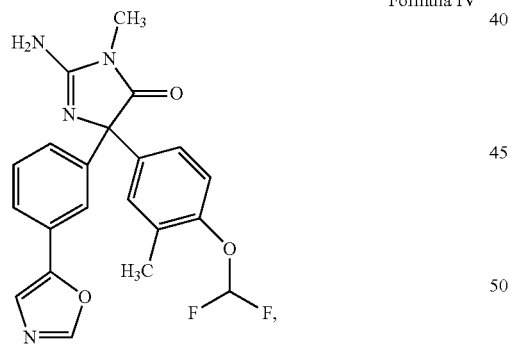

Formula V
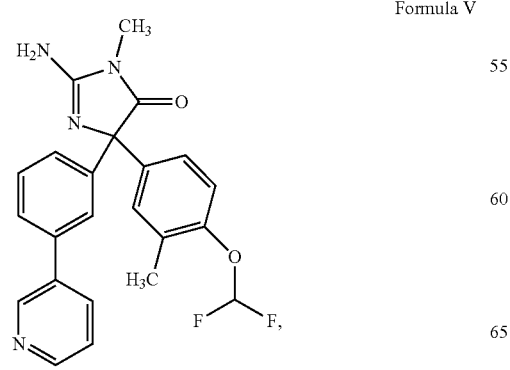

Formula VI
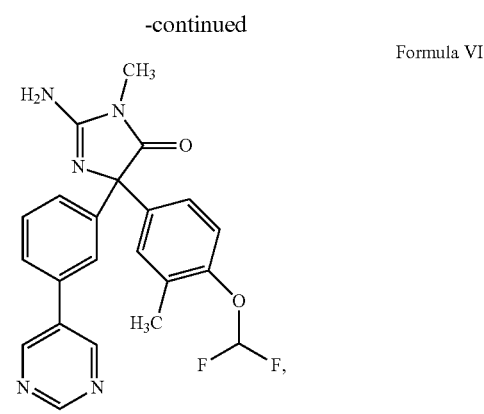

Formula VII
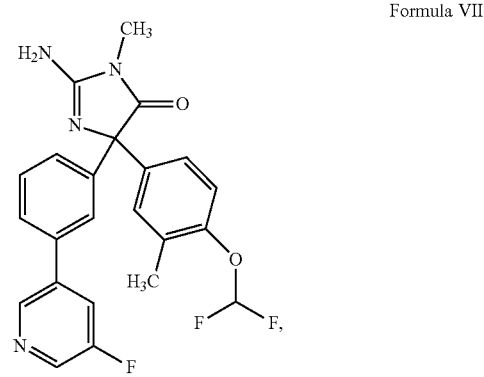 [SMILES: Cc1cc(C2(c3cccc(-c4cncc(F)c4)c3)N=C(N)N(C)C2=O)ccc1OC(F)F]

Formula VIII
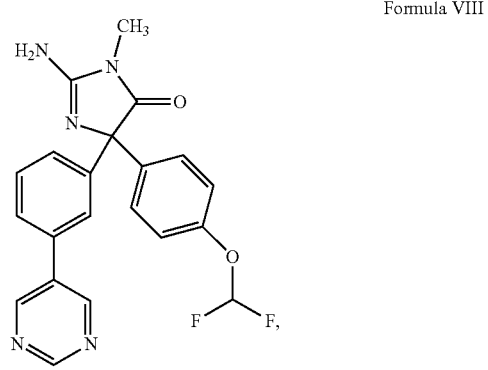

-continued

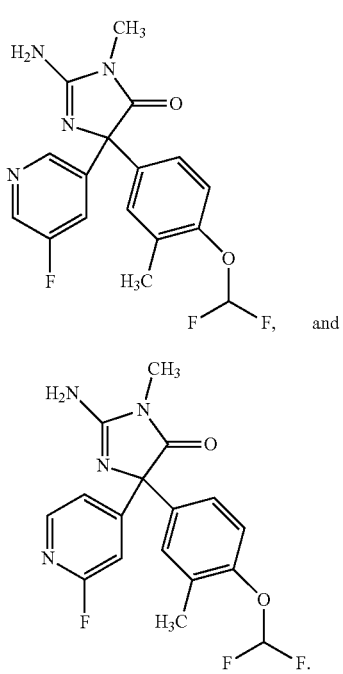

Formula IX and

Formula X

2. The compound according to claim 1, wherein the compound is the compound of formula IV:

(IV)

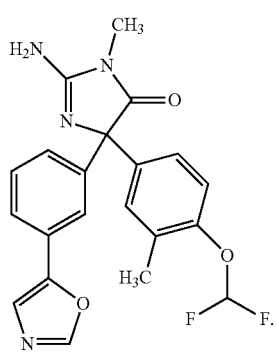

3. The compound according to claim 1, wherein the compound of formula V:

(V)

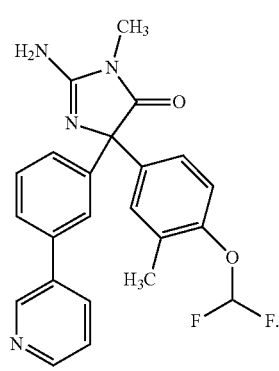

4. The compound according to claim 1, wherein the compound is the compound of formula VI:

(VI)

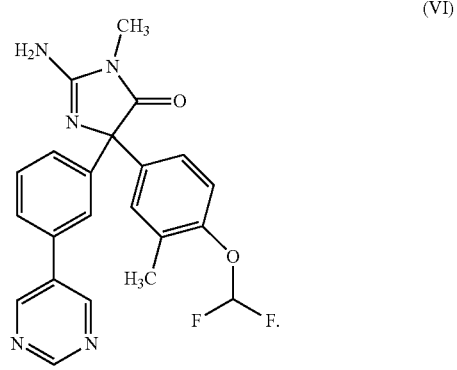 [SMILES: Cc1cc(C2(c3cccc(-c4cncnc4)c3)N=C(N)N(C)C2=O)ccc1OC(F)F]

5. The compound according to claim 1, wherein the compound is the compound of formula VII:

(VII)

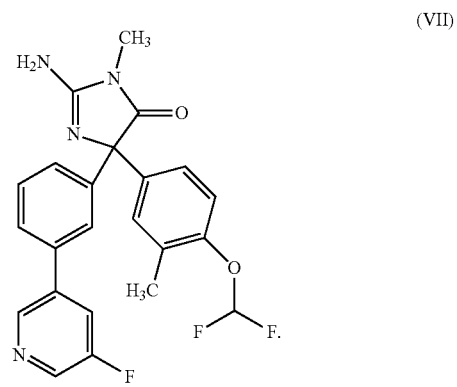 [SMILES: Cc1cc(C2(c3cccc(-c4cncc(F)c4)c3)N=C(N)N(C)C2=O)ccc1OC(F)F]

6. The compound according to claim 1, wherein the compound is the compound of formula VIII:

(VIII)

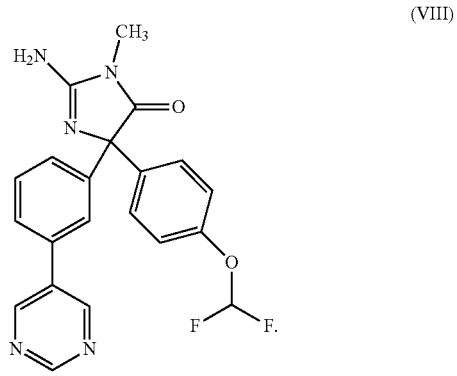 [SMILES: CN1C(=O)C(c2ccc(OC(F)F)cc2)(c2cccc(-c3cncnc3)c2)N=C1N]

7. The compound according to claim 1, wherein the compound is the compound of formula IX:

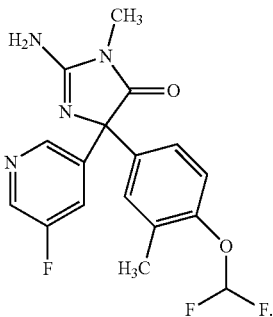

(IX)

8. The compound according to claim 1, wherein the compound is the compound of formula X:

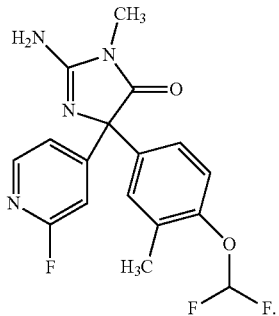

(X)

9. A pharmaceutical composition, comprising a compound according to claim 1 and a pharmaceutically acceptable carrier.

10. The pharmaceutical composition of claim 9, wherein the compound is present in an amount effective to inhibit BACE in a patient when administered to the patient.

11. The pharmaceutical composition of claim 9, wherein the composition is formulated for oral administration or injection.

12. A pharmaceutical composition, comprising a compound according to claim 2 and a pharmaceutically acceptable carrier.

13. A pharmaceutical composition, comprising a compound according to claim 3 and a pharmaceutically acceptable carrier.

14. A pharmaceutical composition, comprising a compound according to claim 4 and a pharmaceutically acceptable carrier.

15. A pharmaceutical composition, comprising a compound according to claim 5 and a pharmaceutically acceptable carrier.

16. A pharmaceutical composition, comprising a compound according to claim 6 and a pharmaceutically acceptable carrier.

17. A pharmaceutical composition, comprising a compound according to claim 7 and a pharmaceutically acceptable carrier.

18. A pharmaceutical composition, comprising a compound according to claim 8 and a pharmaceutically acceptable carrier.

19. A method of treating Alzheimer's Disease, comprising administering a compound according to claim 1 to a patient in need thereof.

20. The method of claim 19, further comprising administering an additional second pharmaceutical agent for treatment of Alzheimer's Disease.

* * * * *